United States Patent
Saito et al.

(10) Patent No.: US 8,045,146 B2
(45) Date of Patent: Oct. 25, 2011

(54) METHOD AND APPARATUS FOR REVIEWING DEFECT

(75) Inventors: Keiya Saito, Hiratsuka (JP); Yasuhiro Yoshitake, Yokohama (JP); Shunichi Matsumoto, Yokohama (JP); Hidetoshi Nishiyama, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 450 days.

(21) Appl. No.: 12/141,955

(22) Filed: Jun. 19, 2008

(65) Prior Publication Data

US 2009/0002695 A1 Jan. 1, 2009

(30) Foreign Application Priority Data

Jun. 22, 2007 (JP) ................................. 2007-164834

(51) Int. Cl.
  *G01N 21/00* (2006.01)
  *G01J 4/00* (2006.01)
(52) U.S. Cl. ..................................... 356/237.2; 356/369
(58) Field of Classification Search ........................ None
See application file for complete search history.

(56) References Cited

U.S. PATENT DOCUMENTS

| | | | |
|---|---|---|---|
| 6,327,025 B1 * | 12/2001 | Imai | 355/53 |
| 6,407,373 B1 | 6/2002 | Dotan | |
| 6,678,043 B1 * | 1/2004 | Vurens et al. | 356/237.2 |
| 7,019,294 B2 * | 3/2006 | Koyama et al. | 250/311 |
| 7,260,256 B2 * | 8/2007 | Hiroi et al. | 382/141 |
| 7,601,954 B2 * | 10/2009 | Nishiyama et al. | 356/237.4 |
| 2005/0087686 A1 * | 4/2005 | Honda et al. | 250/307 |
| 2005/0122508 A1 | 6/2005 | Uto et al. | |
| 2007/0057184 A1 | 3/2007 | Uto et al. | |
| 2007/0121106 A1 * | 5/2007 | Shibata et al. | 356/237.2 |
| 2007/0230768 A1 * | 10/2007 | Adler et al. | 382/144 |

FOREIGN PATENT DOCUMENTS

| | | |
|---|---|---|
| JP | 5-41194 | 2/1993 |
| JP | 7-325041 | 12/1995 |
| JP | 2001-133417 | 5/2001 |
| JP | 2003-7243 | 1/2003 |
| JP | 2005-156537 | 6/2005 |
| JP | 2007-71803 | 3/2007 |

* cited by examiner

*Primary Examiner* — Gregory J Toatley
*Assistant Examiner* — Juan D Valentin
(74) *Attorney, Agent, or Firm* — Antonelli, Terry, Stout & Kraus, LLP.

(57) ABSTRACT

The present invention provides an apparatus and a method for reviewing a defect with high throughput by detecting the defect to be reviewed with high sensitivity, comprising: an optical microscope; a correction means; and a scanning electron microscope which reviews the existing defect on the sample; wherein the optical microscope has: an optical height detection system which optically detects a vertical position of an upper surface of the sample placed on the stage; an illumination optical system which illuminates the defect with light; an image detection optical system which converges and detects reflected light or scattered light generated from the defect illuminated by the illumination optical system to obtain an image signal; and a focus adjusting means which adjusts a focus position of the optical microscope based on the vertical position of the upper surface of the sample, which is detected by the optical height detection system.

9 Claims, 12 Drawing Sheets

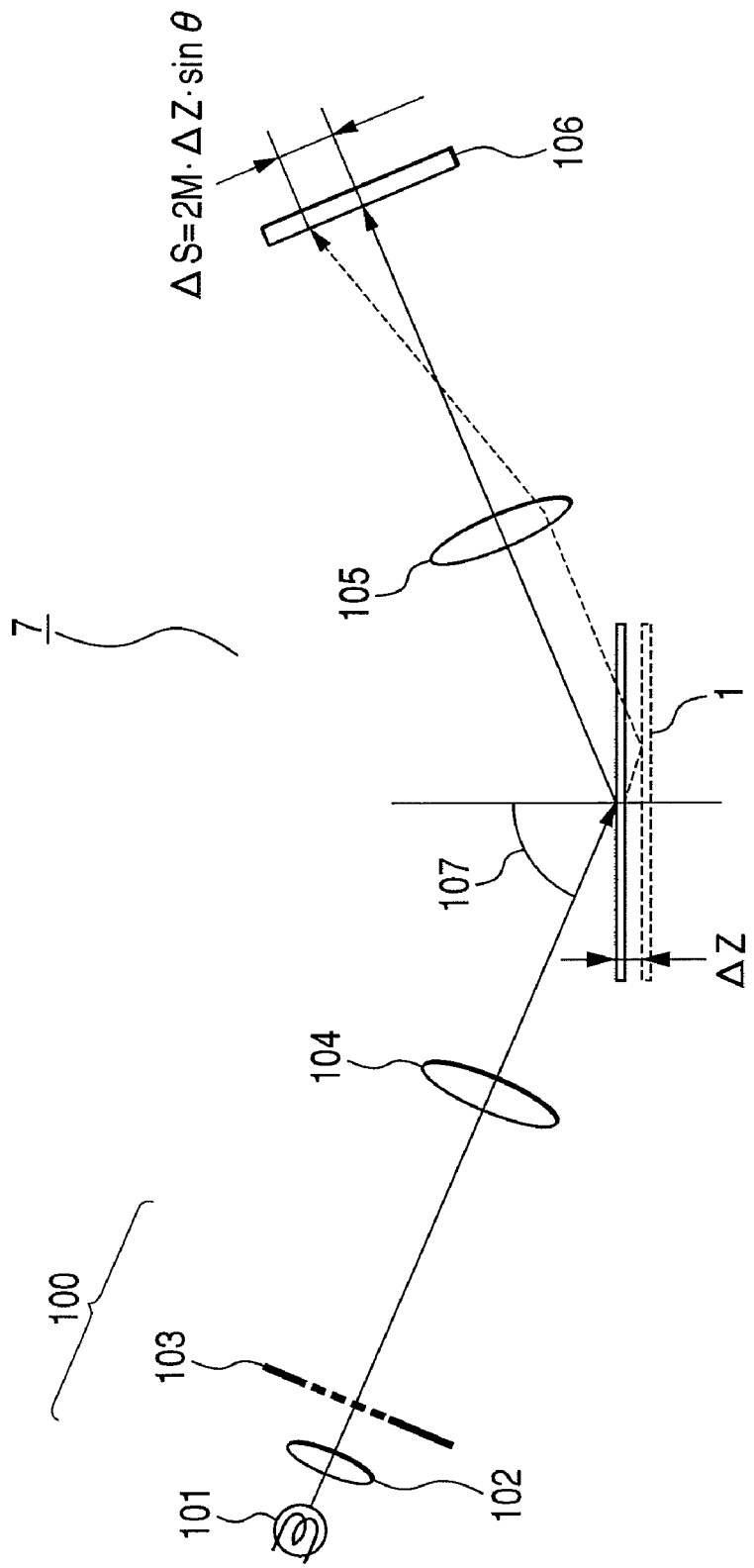

METHOD AND APPARATUS FOR REVIEWING DEFECT

BACKGROUND OF THE INVENTION

The present invention relates to a method and an apparatus for reviewing a defect occurring on a sample such as a semiconductor wafer in a process for manufacturing a semiconductor, and more particularly to a method and an apparatus for reviewing a defect detected by an external optical inspection apparatus by using a scanning electron microscope (SEM) in detail.

When a defect such as a foreign material is existed on a semiconductor substrate (wafer) in a process for manufacturing a semiconductor, a circuit failure may occur. The circuit failure includes insufficient insulation and a short circuit occurring in a wiring connection. In accordance with a semiconductor device miniaturization, a minute defect may cause a capacitor to be insufficiently insulated or a gate oxide film to be broken. Defects may be introduced into a sample in various states due to various causes. For example, a defect may be introduced into a sample from a movable part of a carrier device, a human body, a chemical or a material, or may be a product generated by reaction with a process gas present in a process device. To avoid the problem, it is necessary to change process conditions or improve equipment for manufacturing semiconductors, by detecting a defect occurring on a semiconductor substrate in the manufacturing process and finding the source of the defect.

In a conventional method for detecting the source of a defect, an external optical inspection apparatus specifies the position of the defect, and a scanning electron microscope (SEM) or the like reviews the defect in detail and classify the defect. Then, information of the defect reviewed in detail and classified is compared with information present in a database, and the cause of the defect is estimated based on the comparison.

The external optical inspection apparatus is an optical foreign material inspection apparatus or an optical appearance inspection apparatus. The optical foreign material inspection apparatus is adapted to detect light scattered from the defect to specify the position of the defect. The optical appearance inspection apparatus is adapted to detect a bright field optical image of a semiconductor substrate by using lamp light or laser light as illumination light to compare the optical image with reference information thereby specifying the position of the defect on the semiconductor substrate.

Such reviewing methods are disclosed in JP-A-2001-133417 corresponding to U.S. Pat. No. 6,407,373 B1, JP-A-7-325041, JP-A-2003-7243, JP-A-5-41194, JP-A-2005-156537 corresponding to US 2005/0122508 A1 and JP-A-2007-71803 corresponding to US 2007/0057184 A1.

To detect a defect present on a semiconductor substrate by using an optical foreign material inspection apparatus with high inspection throughput, laser light is irradiated on the semiconductor substrate with a large spot to scan the substrate and detect the defect. This results in the fact that information on the position of the defect, which is obtained based on the position of the laser spot to scan the semiconductor circuit, includes a large error component.

When the defect is reviewed by a scanning electron microscope in detail with higher magnification (a smaller visual field) than that of an optical system of the external optical inspection apparatus based on rough position information of the defect with the error component, the reviewed defect may not fall within the visual field of the scanning electron microscope. To cause the defect (to be reviewed) to fall within the visual field of the scanning electron microscope, the defect is searched while the visual field of the scanning electron microscope is changed. This takes a long time since the visual field is small, resulting in a reduction in the throughput of the scanning electron microscope and an increase in the time for analyzing the defect.

JP-A-2001-133417 discloses an apparatus for reviewing a defect arranging both a scanning electron microscope and an optical microscope to solve the abovementioned problem. In the apparatus described in JP-A-2001-133417, the optical microscope redetects a defect and specifies the position of the defect, and the scanning electron microscope reviews the defect in detail. It is general that when a numerical aperture of an objective lens provided in the optical microscope is increased in order to detect a foreign material with high sensitivity, a focal depth of the optical microscope is reduced. This results in difficulty in the focusing operation of the optical microscope. In JP-A-2001-133417, it touches about a focusing operation of the optical microscope. JP-A-2001-133417, however, does not provide a sufficient description of the focusing operation of the optical microscope. JP-A-2005-156537 describes a focusing method. In the focusing method described in JP-A-2005-156537, a position in a Z-direction at which in a plurality of dark field images detected by moving a Z-stage step-by-step in predetermined displacements in the Z-direction, a luminance value of the detected dark field image is the maximum is deemed as a just-in-focus position. In the focusing method, however, when a numerical aperture of an objective lens provided in an optical microscope is increased, a focal depth of the optical microscope is reduced. This results in the fact that it is necessary to reduce the displacement of step-by-step for acquiring a dark field image. The throughput of the focusing operation is therefore reduced.

In addition, it is difficult to detect a foreign material on a metal film with high sensitivity by an optical microscope as a defect present on a semiconductor substrate, even when the numerical aperture of an optical system provided in the optical microscope is large.

SUMMARY OF THE INVENTION

It is an object of the present invention to provide an apparatus and a method for reviewing a defect with high throughput by detecting the defect to be reviewed with high sensitivity by an optical microscope and causing the defect to securely fall (put) within a visual field of a scanning electron microscope (SEM) or the like.

An apparatus for reviewing a defect, according to a first aspect of the present invention, comprising:

an optical microscope which optically re-detects a existing defect on a sample placed on the stage provided in a vacuum chamber, which has been detected by an external optical inspection apparatus beforehand, and obtains at least position information of the existing defect on the sample;

a correction means which corrects position information of the existing defect on the sample which has been detected by the external optical inspection apparatus beforehand, based on the position information obtained by optically re-detecting the existing defect on the sample with the optical microscope; and a scanning electron microscope which reviews the existing defect on the sample by positioning the existing defect on the sample within a visual field of the scanning electron microscope by moving the stage based on the position information of the defect corrected by the correction means, wherein the optical microscope has:

an optical height detection system which optically detects a vertical position of an upper surface of the sample placed on the stage;

an illumination optical system which illuminates the existing defect on the sample with light; an image detection optical system which converges and detects reflected light or scattered light generated from the existing defect on the sample illuminated by the illumination optical system to obtain an image signal; and a focus adjusting means which adjusts a focus position of the optical microscope based on the vertical position of the upper surface of the sample, which is detected by the optical height detection system.

An apparatus for reviewing a defect, according to a second aspect of the present invention, comprising:

an optical height detection system which optically detects a vertical position of an upper surface of a sample placed on the stage;

an optical microscope which optically re-detects a existing defect on the sample placed on the stage provided in a vacuum chamber, which has been detected by an external optical inspection apparatus beforehand, and obtains position information of the existing defect on the sample;

a correction means which corrects position information of the existing defect on the sample which has been detected by the external optical inspection apparatus beforehand, based on the position information obtained by optically re-detecting the existing defect on the sample with the optical microscope; and a scanning electron microscope which reviews the existing defect on the sample placed on the stage by positioning the existing defect on the sample within a visual field of the scanning electron microscope by moving the stage based on the position information of the defect corrected by the correction means, wherein the optical microscope has:

an illumination optical system which illuminates the existing defect on the sample with light;

an image detection optical system which converges and detects reflected light or scattered light generated from the existing defect on the sample illuminated by the illumination optical system to obtain an image signal; and a focus adjusting means which adjusts a focus position of the optical microscope based on the vertical position of the upper surface of the sample, which is detected by the optical height detection system.

According to the present invention, a defect to be reviewed is detected with high sensitivity by means of the optical microscope, and the defect surely falls within the visual field of the scanning electron microscope or the like in a short time. This increases throughput of the detail inspection of a defect.

These and other objects, features and advantages of the invention will be apparent from the following more particular description of preferred embodiments of the invention, as illustrated in the accompanying drawings.

BRIEF DESCRIPTION OF THE DRAWINGS

FIG. 9 is a diagram showing an example of an outline construction of a scanning electron microscope (SEM) height detection system for the scanning electron microscope;

DESCRIPTION OF THE PREFERRED EMBODIMENTS

A description will be made of an apparatus for reviewing a defect according to each of embodiments of the present invention with reference to the accompanying drawings.

First Embodiment

Figure 1:
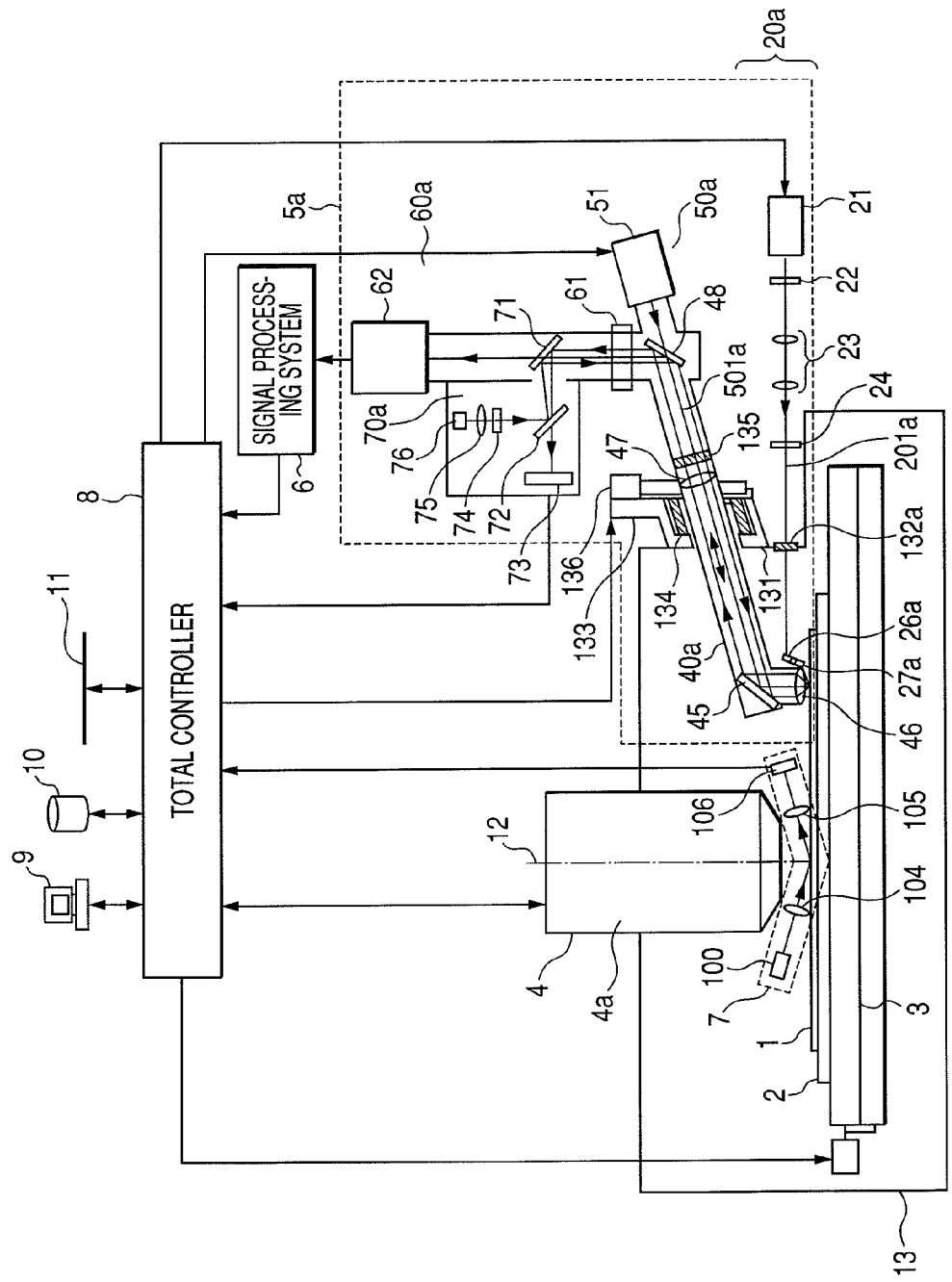
FIG. 1 is a diagram showing an outline construction of an apparatus for reviewing a defect according to a first embodiment of the present invention.

FIG. 1 shows the construction of the apparatus for reviewing a defect according to a first embodiment of the present invention. The apparatus is comprised by mounting (arranging) an optical microscope 5a in a scanning electron microscope (SEM) 4. The scanning electron microscope (SEM) 4 reviews a defect present on a sample 1 in detail and classify the defect based on a highly magnified electron image (a secondary electron image or a reflected electron image) obtained by irradiating so as to scan an electron beam on the sample 1 such as a semiconductor wafer. The optical microscope 5 optically redetects the existing defect on the sample 1 to obtain precise position information of the defect. The apparatus according to the present invention is further comprised an XY stage 3, a vacuum chamber (vacuum sample chamber) 13, a signal processing system 6, a height detection system 7 of the scanning electron microscope (SEM), and a total controller 8. The XY stage 3 holds a sample holder 2 and is movable. The sample holder 2 holds the sample 1 such as a semiconductor wafer, which is to be inspected. A microscope tube 4a of the scanning electron microscope (SEM) 4 and an edge portion of a microscope tube 40a of the optical microscope 5a are provided in the vacuum chamber 13. The signal processing system 6 acquires the precise position information of a defect based on an image signal output from an optical detector 62. The optical detector 62 is comprised of a two-dimensional charge coupled device (CCD) camera or the like and provided in an optical detection system 60a of the optical microscope 5a. The SEM height detection system 7 is provided in the vacuum chamber 13 and detects a vertical position of an upper surface of the sample 1 on an optical axis 12 of the scanning electron microscope 4. The total controller 8 controls the entire sequence of operations to be performed in the apparatus according to the first embodiment and is connected to an input/output terminal 9, a database 10 and a network 11.

In the scanning electron microscope (SEM) 4, an electron gun (not shown) emits an electron beam, and a condenser lens (not shown) and an objective lens (not shown) irradiates by condensing the electron beam emitted from the electron gun onto the sample 1. The electron beam scans a region of the sample 1, which is set by a deflection electrode (not shown). A detector (not shown) detects a secondary electron generated from the sample 1 or an electron reflected from the sample 1 to obtain a highly magnified electron image based on the secondary electron or the reflected electron.

The optical microscope 5a includes a dark field illumination optical system 20a, a bright field illumination optical system 50a, an optical detection system 60a, and a height detection system 70a of the optical microscope (OM). The dark field illumination optical system 20a performs dark field illumination in which light is output from a prism 27a provided at the edge portion of the microscope tube 40a onto the upper surface of the sample 1. The bright field illumination optical system 50a performs bright field illumination in which light is output from the microscope tube 40a onto the upper surface of the sample 1. The optical detection system 60a detects an image represented by light reflected from a existing defect on the sample 1 through the microscope tube 40a to obtain an image signal. The OM height detection system 70a optically detects a vertical position of the upper surface of the sample 1 through the microscope tube 40a. The vertical position of the upper surface of the sample 1 is measured in a direction parallel to the normal to an upper surface of the XY stage 3.

A portion of the bright field illumination optical system 50a, a portion of the optical detection system 60a and a portion of the OM height detection system 70a are shared with the microscope tube 40a. The microscope tube 40a has an objective lens 46, a mirror (an optical element) 45, an imaging lens 47 and a beam splitter 48. The objective lens 46 converges light from the side of the edge portion of the microscope tube 40a. The mirror 45 is adapted to change propagation of light. The prism 27a (reflecting optical element) is to be used for the dark field illumination. The prism 27a is provided in the microscope tube 40a and on the side of the edge portion of the microscope tube 40a. A prism (mirror) 26a (reflecting optical element) is to be used for the dark field illumination. The prism 26a is fixed to the vacuum chamber 13. The microscope tube 40a is movable in a Z direction (vertical direction) by means of a Z actuator 136. The Z direction is parallel to the normal to the upper surface of the XY stage 3. A bellows 134 is provided to maintain vacuum within the vacuum chamber 13.

The dark field illumination optical system 20a includes a laser light source 21, a shutter 22, a beam diameter changing (beam expander) unit 23, a wavelength plate 24, and the prisms 26a and 27a. The laser light source 21 emits a visible laser beam having wavelengths of 532 nm, 488 nm, 405 nm and the like and an ultraviolet laser beam having wavelengths of 355 nm and the like. The shutter 22 is adapted to pass and block the laser beam output from the laser light source 21 based on a command output from the total controller 8. The beam diameter changing unit 23 changes the diameter of the laser beam. The wavelength plate 24 adjusts a polarization direction of the laser beam. Each of the prisms 26a and 27a reflects the laser beam, which has passed a vacuum blocking glass 132a and been introduced into the vacuum chamber 13, and changes the direction of propagation of the laser beam. The prisms 26a and 27a output the laser beam onto the surface of the sample 1 from a direction inclined to the normal to the upper surface of the XY stage to ensure that dark field illumination is performed. Since the prism 26a is fixed to the vacuum chamber 13, the prism 26a does not move even when the position of the microscope tube 40a is adjusted in the vertical direction (even when a focusing position of the optical microscope 5a is adjusted). It should be noted that the shorter the wavelength of the laser beam emitted by the laser light source 21, the higher the sensitivity of detection of a defect.

The bright field illumination optical system 50a is used to adjust (align) the position of the sample 1. The bright field illumination optical system 50a includes a bright field illumination light source 51 composed of, for example, a halogen lamp, which emits white light. The optical detection system 60a includes a polarization detector (analyzer) 61 and the optical detector 62 composed of the two-dimensional CCD camera or the like.

The OM height detection system 70a includes a semiconductor laser 76, a collimate lens 75, a slit plate 74, a beam splitter 72, a dichroic mirror 71 and a position sensor 73. The collimate lens 75 collimates a laser beam output from the semiconductor laser 76. The slit plate 74 receives the collimated laser beam and forms a slit beam to be projected onto the sample 1. The position sensor 73 detects the vertical position of the upper surface of the sample 1 based on focus positions of slit beam images obtained from the sample 1. In the OM height detection system 70a, the semiconductor laser 76 outputs a laser beam. The collimate lens 75 collimates the laser beam output from the semiconductor laser 76 and outputs the collimated laser beam to the slit plate 74. The slit plate 74 receives the collimated laser beam from the collimate lens 75 and forms a slit beam. The slit beam output from the slit plate 74 passes through the beam splitter 72, the dichroic mirror 71, and the beam splitter 48. The slit beam enters from the beam splitter 48 into the microscope tube 40a. The slit beam then passes through the vacuum blocking glass 135, the imaging lens 47, the mirror 45, and the objective lens 46. The slit beam is then projected onto the sample 1 to form a slit image on the sample 1. The slit image projected onto the sample 1 is reflected on the sample 1. The reflected slit image propagates in the order opposite to the order of the incidence on the sample 1. That is, the reflected slit image passes through the objective lens 46, the mirror 45, the imaging lens 47, the vacuum blocking glass 135, the beam splitter 48, the dichroic mirror 71, and the beam splitter 72. The reflected slit image is then imaged on the position sensor 73. The position sensor 73 detects a distance Δz from in-focus position of the upper surface of the sample 1 on an optical axis of the lenses 46 and 47, based on the position (displacement) Δs of the slit beam imaged on the position sensor 73.

Figure 2:
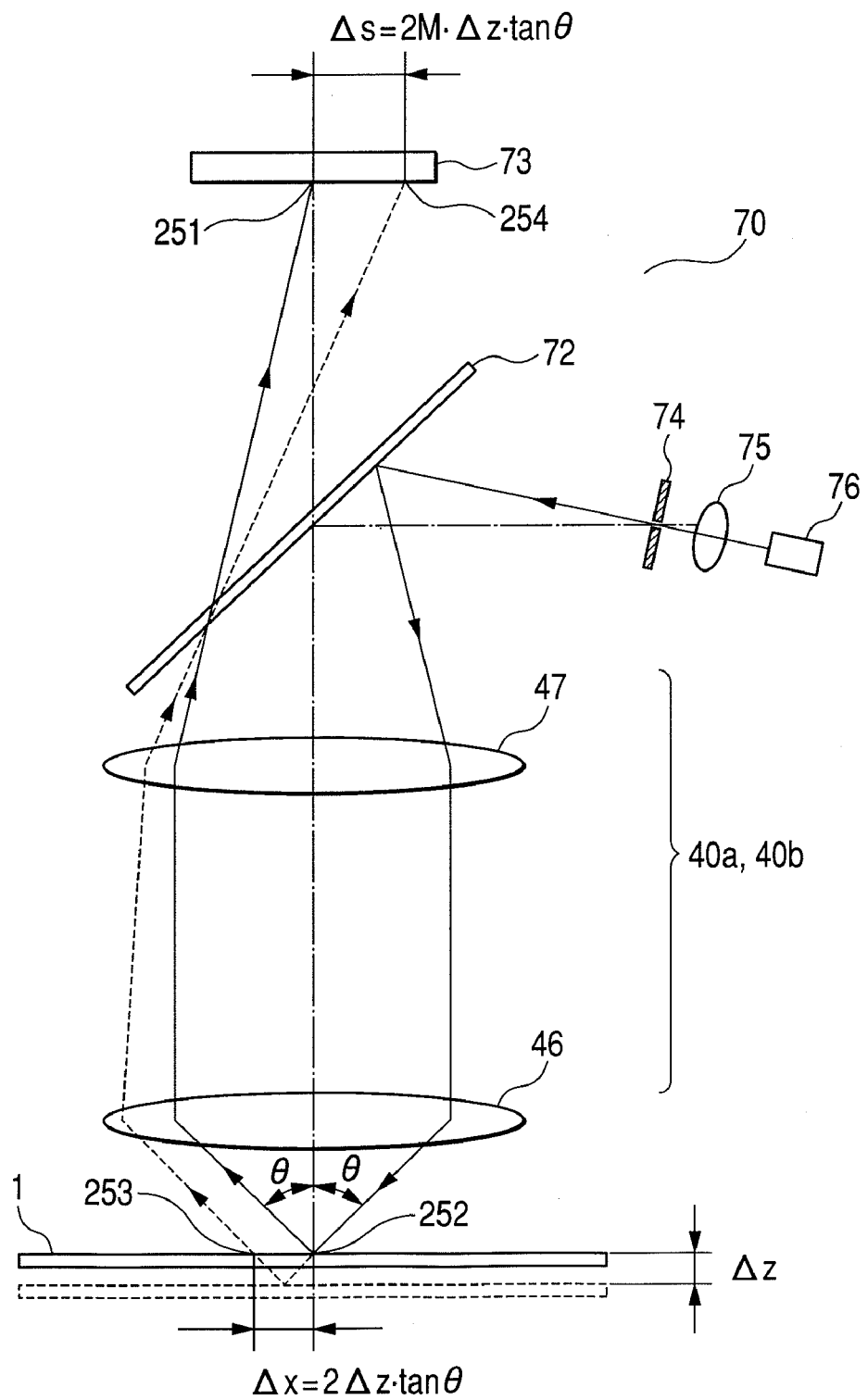
FIG. 2 is a diagram showing an example of an outline construction of an optical height detection system of an optical microscope provided in the apparatus according to the first embodiment.

Next, a description will be made of details of a method for detecting the vertical position of the upper surface of the sample 1 on the optical axis of the lenses 46 and 47 by the OM height detection system 70a with reference to FIG. 2. In FIG. 2, the dichroic mirror 71, the beam splitter 48, the vacuum blocking glass 135 and the mirror 45 are not drawn since they are not involved in the imaging. FIG. 2 shows the case where the upper surface of the sample 1 is the same as the in-focus position and the case where the upper surface of the sample 1 is lower by a distance (height) Δz than the in-focus position on the optical axis of the lenses 46 and 47. The position of the slit plate 74 is conjugated with the in-focus position of the sample 1. The in-focus position of the sample 1 is conjugated with the position of the position sensor 73. When the upper surface of the sample 1 is the same as the in-focus position on the optical axis of the lenses 46 and 47, the slit beam projected by the slit plate 74 is reflected on the upper surface of the sample 1 and imaged on the center 251 of the position sensor 73. On the other hand, when the upper surface of the sample 1 is lower by the distance (height) Δz than the in-focus position, the beam reflected on the sample 1 passes through a point 253 which is sifted by a value Δx (=2Δz·tan θ) from the position 252 present on the upper surface of the sample 1 and reaches a point 254 which is sifted by a value Δs (=2M·Δz·tan θ) from the center 251 of the position sensor 73. The value M is magnification of the optical microscope 5a and is defined by the imaging lens 47 and the objective lens 46.

Figure 3:
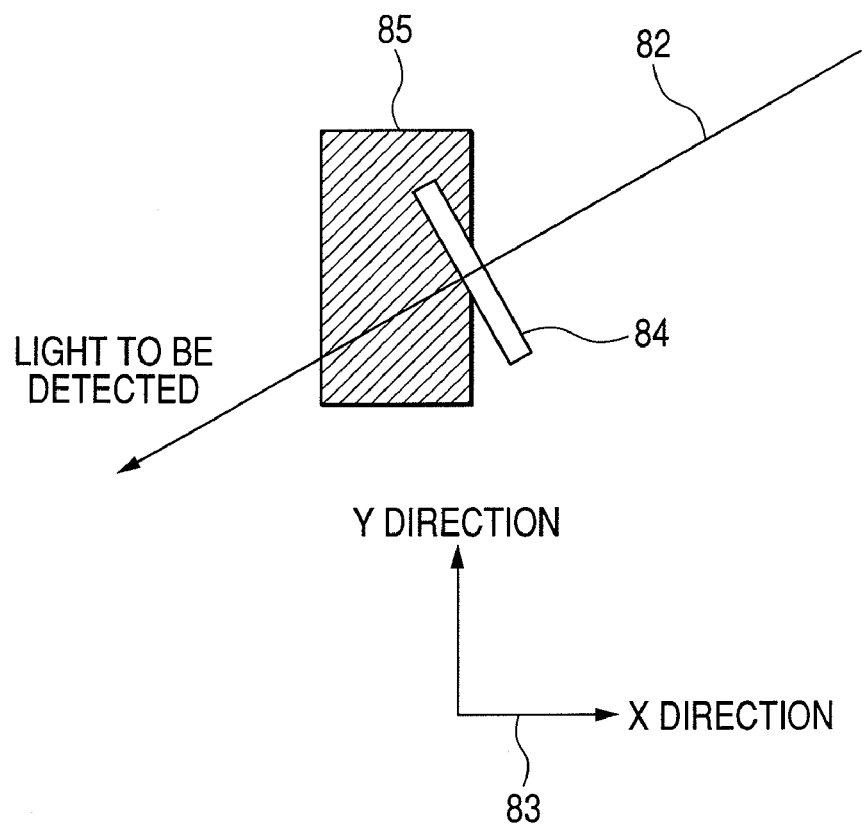
FIG. 3 is a diagram showing the relationship between a pattern of a sample detected by an OM height detection system shown in FIG. 2 and slit light.

It is, therefore, possible to detect the value Δz (which indicates the vertical position of the upper surface of the sample 1 distant by the value Δz from the in-focus position 252 on the optical axis of the lenses 46 and 47) by detecting the shifted value Δs (from the center 251 to the center of gravity of the slit beam imaged on the position sensor 73). When a pattern is existed on the upper surface of the sample 1, a difference of reflectance of the slit beam reflected on a boundary portion of the pattern is generated. Due to the difference of the reflectance, the intensity distribution of the beam to be detected may be varied (distorted), resulting in the fact that the detected vertical position of the sample includes an erroneous value. To reduce the erroneous value, the OM height detection system 70a is arranged to ensure that the incident direction 82 of the slit beam is inclined at a certain angle with respect to an X direction 83 of movement of the XY stage 3 as shown in FIG. 3. This arrangement leads to the fact that a slit image 84 crosses only a part of a boundary portion of a pattern 85 existed on the surface of the sample 1. This reduces an error occurring due to the boundary portion of the pattern. Information on the vertical position of the upper surface of the sample 1, which is obtained by the OM height detection system 70a, is input to the total controller 8. The total controller 8 causes the optical detection system 60a provided in the optical microscope 5a to move based on the focus position of the optical microscope 5a. Thus, the microscope tube 40a is moved by the Z actuator 136 in the Z direction (vertical direction) so as to in-focus the objective lens 46 provided at the edge portion of the microscope tube 40a whereby the upper surface of the sample 1 is adjusted to the in-focus position. In this case, the prism 27a is slightly moved with the objective lens 46 in the vertical direction since the prism 27a is fixed to the edge portion of the microscope tube 40a.

Under the condition that the upper surface of the sample 1 is focused to the in-focus position like this, the optical microscope 5a performs a dark field detection using the dark field illumination optical system 20a and the optical detection system 60a in order to obtain precise position information of a existing defect on the sample by re-detecting the defect. Specifically, the shutter 22 of the dark field illumination optical system 20a is opened based on a command output from the total controller 8. A laser beam (e.g., ultraviolet laser beam) emitted by the laser light source 21 passes through the shutter 22 and reaches the beam diameter changing unit 23. The beam diameter changing unit 23 adjusts the diameter of the laser beam to be illuminated and outputs the adjusted laser beam to the wavelength plate 24. The wavelength plate 24 receives the laser beam from the beam diameter changing unit 23. The wavelength plate 24 then selects a polarization direction of the laser beam to ensure that the laser beam is suitable for detection of a defect with high sensitivity. The wavelength plate 24 then outputs the laser beam through the vacuum blocking glass 132a to the prisms 26a and 27a provided in the vacuum chamber 13. The prisms 26a and 27a change the direction of propagation (optical pass) of the laser beam. The laser beam is then irradiated on the upper surface of the sample 1 from a direction inclined to the normal to the upper surface of the sample 1. To detect the defect with high sensitivity, for example, an S-polarized laser beam is selected when the size of a foreign material (which is a defect) is relatively large, and a P-polarized laser beam is selected when the size of the foreign material is relatively small. After the laser beam is irradiated on the upper surface of the sample 1, an image represented by light scattered from the defect is converged by the objective lens 46 provided in the microscope tube 40a. The mirror 45 changes a direction of propagation of the light converged by the objective lens 46. The image is imaged on the optical detector 62 by the imaging lens 47 through the vacuum blocking glass 135, the beam splitter 48 and the dichroic mirror 71.

Figure 4:
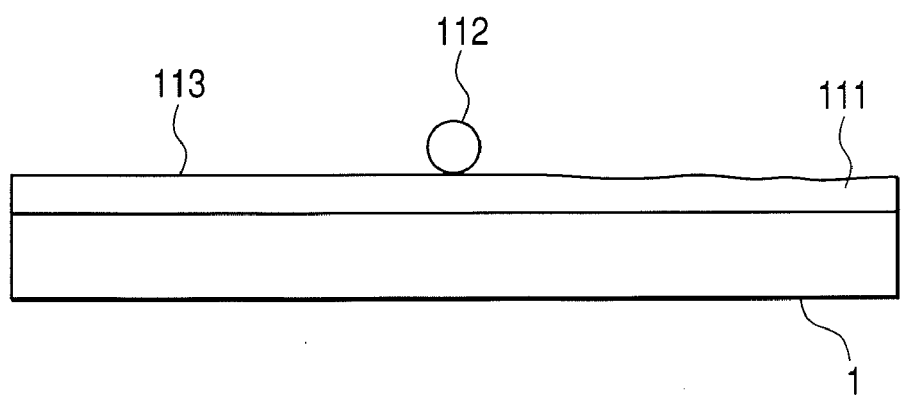
FIG. 4 is a diagram showing a structure of a sample to be subjected to polarization detection by means of the optical microscope.

Next, the polarization detector (analyzer) 61 will be described with reference to FIGS. 4 to 7. The polarization detector 61 has a polarization plate inserted therein to detect polarized light. The polarization detector 61 is designed to ensure that a defect is detected with higher sensitivity than that of detection in the case where non-polarized light is detected. The polarization detector 61 can be used in the case where a foreign material existed on a metal film is to be detected. FIG. 4 shows the case where a metal film 111 is formed on the sample 1 and a foreign material 112 existed on the metal film 111 is to be detected. When the dark field illumination optical system 20a illuminates the sample 1 shown in FIG. 4 with a laser beam, scattered light is generated from the foreign material 112. In this case, scattered light is generated from an upper surface of the metal film 111 due to roughness of the upper surface of the metal film 111. The intensity of the scattered light due to roughness of the upper surface of the metal film 111 is relatively large. In the case where the foreign material 112 is detected based on the scattered light, the scattered light due to the roughness of the upper surface of the metal film 111 is detected as a noise component. Therefore, since the signal-to-noise ratio (obtained when the foreign material is detected) is reduced, it is impossible to detect the foreign material with high sensitivity.

When an S-polarized laser beam is incident on the sample 1, the scattered light generated from the foreign material 112 includes an S-polarized light component and a P-polarized light component. On the other hand, it is considered that the light reflected on the sample 1 has the same polarization direction as that of the laser beam incident on the sample 1. However, in the case where the metal film 111 is formed on the sample 1, the scattered light due to the roughness of the upper surface of the metal film 111, includes an S-polarized light component and a P-polarized light component. To apply the polarization detection to the detection of the foreign material, it is necessary to select an optimal polarization direction of the light to be incident on the sample 1 and an optimal polarization direction of the scattered light to be detected.

Figure 5:
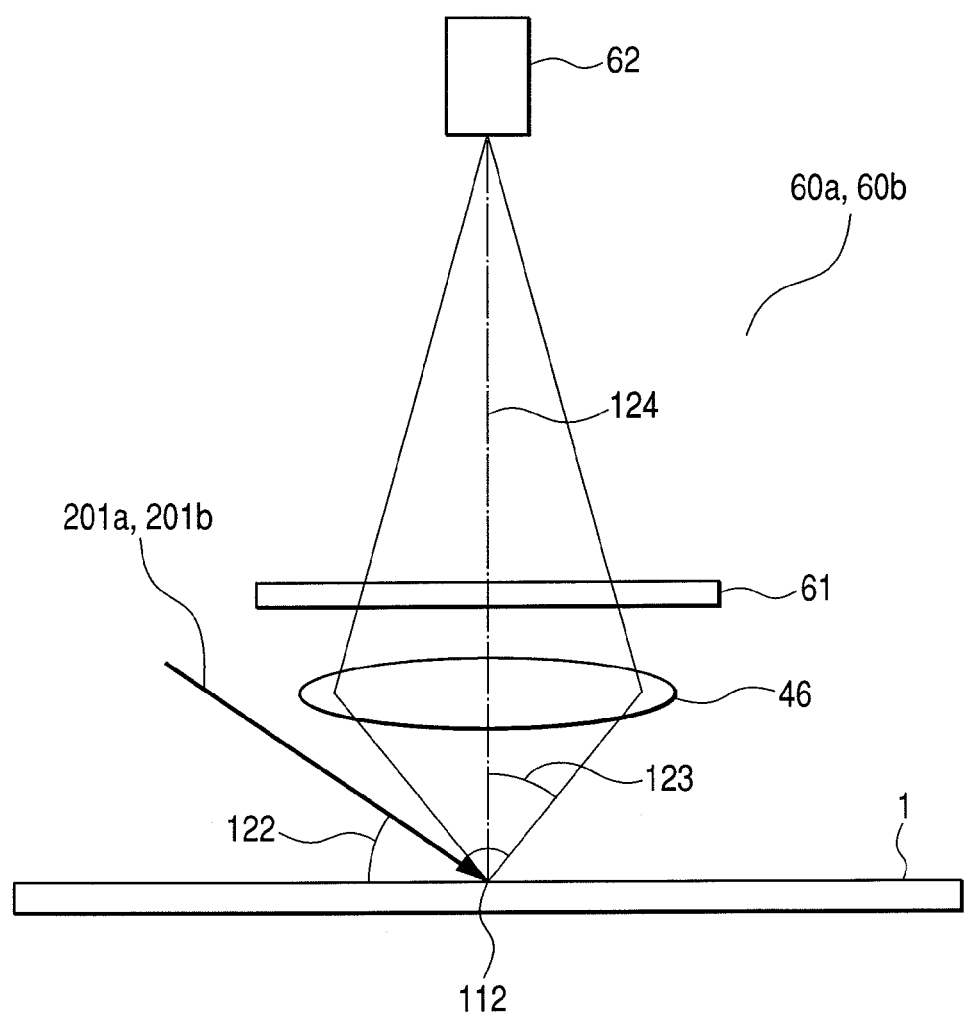
FIG. 5 is an explanatory diagram showing an optical model for simulating the polarization detection by means of the optical detection system of the optical microscope.
Figure 6:
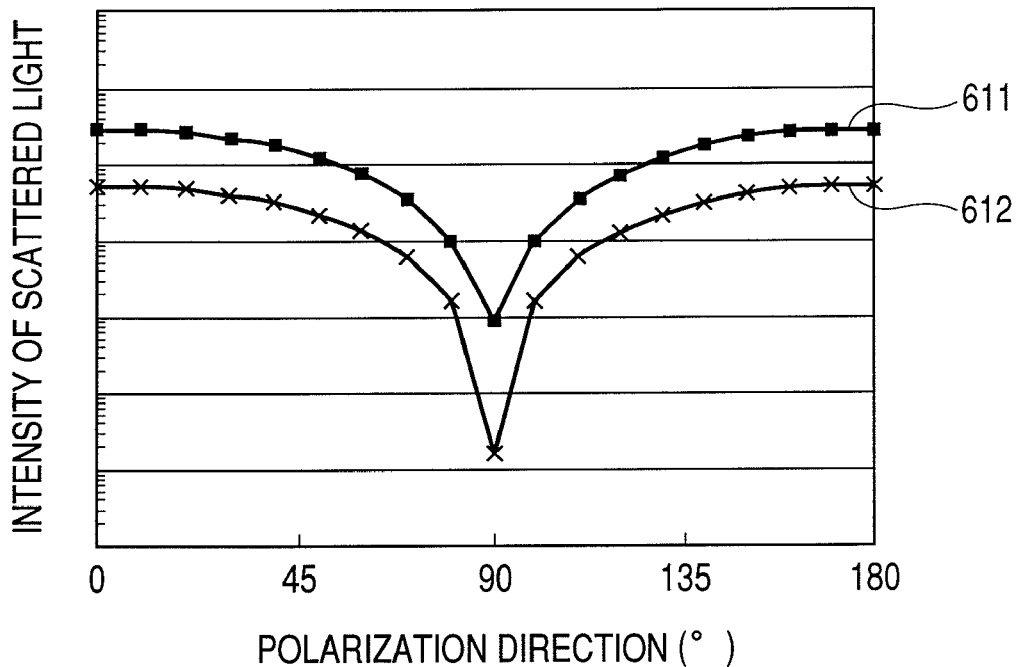
FIG. 6 is a graph showing intensities of scattered light, which are obtained by the simulation based on the optical model shown in FIG. 5.

A simulation is performed using an optical model shown in FIG. 5 to evaluate the signal-to-noise ratio (obtained when the foreign material 112 is detected) in terms of polarization directions of the incident light and the scattered light to be detected. FIG. 5 shows a model of the dark field illumination optical system 20a and the optical detection system 60a, which are provided in the optical microscope 5a shown in FIG. 1. In this model, the following are set: the wavelength of a dark field illumination light 201a; an elevation angle 122 formed between a direction of propagation of the dark field illumination light 201a and the upper surface of the sample 1; a numerical aperture (NA) 123 of the objective lens 46 provided in the microscope tube 40a; a direction 124 of light to be detected by the optical detector 62; the size of the foreign material 112; a material of the metal film 111; and the roughness of the upper surface of the metal film 111. Under the condition that the dark field illumination light 201a is either S-polarized light or P-polarized light and a polarization direction of light detected by the polarization detector 61 is changed, the following light intensities are evaluated: the intensity of scattered light generated from the foreign material 112; and the intensity of scattered light generated from the upper surface of the metal film 111 due to the roughness of the upper surface of the metal film 111. As a result of the evaluation, when the dark field illumination light 201a (incident light) is S-polarized light, and the polarization detector (analyzer) 61 detects a polarization direction of 90 degrees (P-polarization), which is obtained by rotating the polarization direction (of zero degrees) of the incident light by 90 degrees as shown in FIG. 6, the intensity of scattered light 611 generated from the foreign material 112 and the intensity of scattered light 612 generated from the metal film 111 due to the roughness of the upper surface of the metal film 111 are the minimum values, respectively. In this case, the reduction rate of the intensity of the scattered light 612 with respect to the polarization direction is the maximum.

Figure 7:
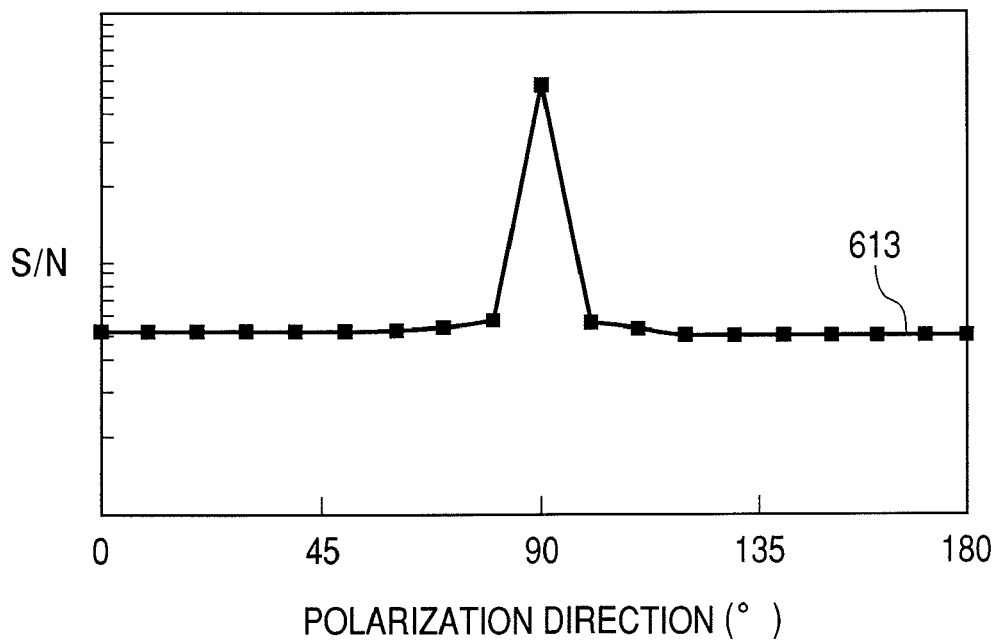
FIG. 7 is a graph showing signal-to-noise ratios obtained by the simulation based on the optical model shown in FIG. 5.

The signal-to-noise ratio (obtained when the foreign material 112 is detected) is calculated based on the ratio of the intensity of the scattered light 611 generated from the foreign material 112 relative to the intensity of the scattered light 612 generated from the metal film 111 due to the roughness of the upper surface of the metal film 111. Referring to FIG. 7, when the polarization detector (analyzer) 61 detects the polarization direction of 90 degrees (P-polarization), the signal-to-noise ratio 613 is the maximum. Each of FIGS. 6 and 7 shows the case where the incident light is S-polarized light. When the incident light is P-polarized light, the signal-to-noise ratio is not increased regardless of the polarization direction of the light detected by the polarization detector 61. To avoid this, for example, the total controller 8 calculates the polarization direction of the incident light and the polarization direction of the light to be detected by the polarization detector 61 to ensure that the signal-to-noise ratio is maximized, based on the size of the foreign material 112, the material of the metal film 111, the roughness of the upper surface of the metal film 111, the polarization direction of the incident light, the polarization direction of the light to be detected, and the like. The calculated data on the polarization directions is registered in the database 10, for example. To detect a defect such as a foreign material existed on a metal film by the optical microscope 5a, the total controller 8 can therefore set conditions suitable for detecting the polarization direction of the light to be detected by the polarization detector (analyzer) 61 based on design information and process information on a semiconductor wafer such as a metal film on which a defect such as a foreign material (detected by an external optical inspection apparatus) is existed. The design information and the process information are input to the total controller 8 from the input/output terminal 9 or through the network 11.

When a repetitive pattern is existed on the sample 1, a spatial filter (not shown) is inserted at a Fourier transform position corresponding to the position of an exit pupil of the objective lens 46 provided in the optical microscope 5a to reduce the amount of light reflected on the repetitive pattern, which acts as noise during the detection of a defect. The spatial filter blocks an image represented by light reflected and diffracted by the repetitive pattern. This makes it possible to detect a existing defect on the repetitive pattern.

Figure 8A:
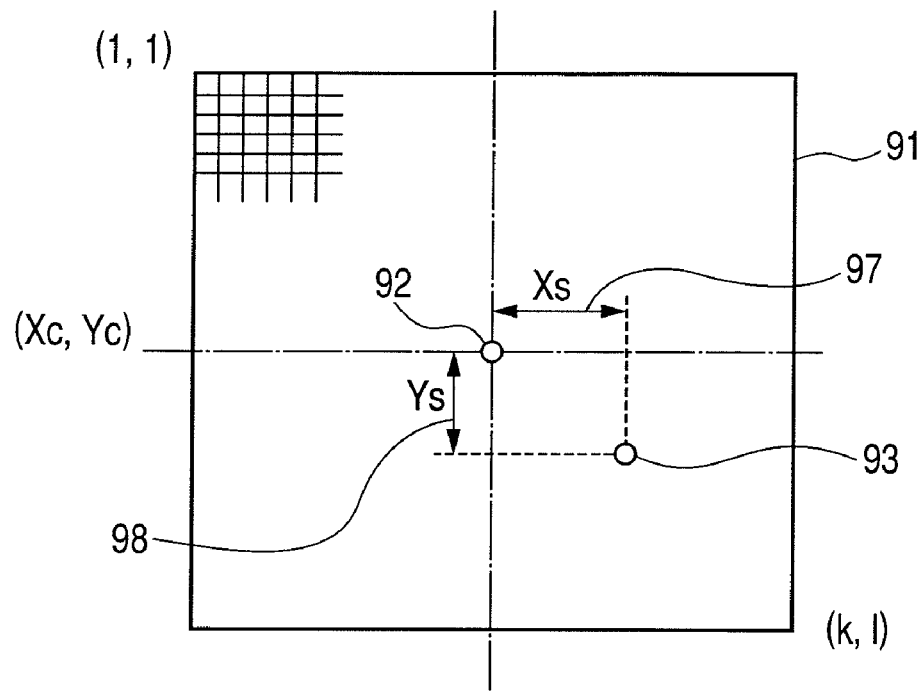
FIG. 8A is a diagram showing a detected image signal when a defect is present across a plurality of pixels.
Figure 8B:
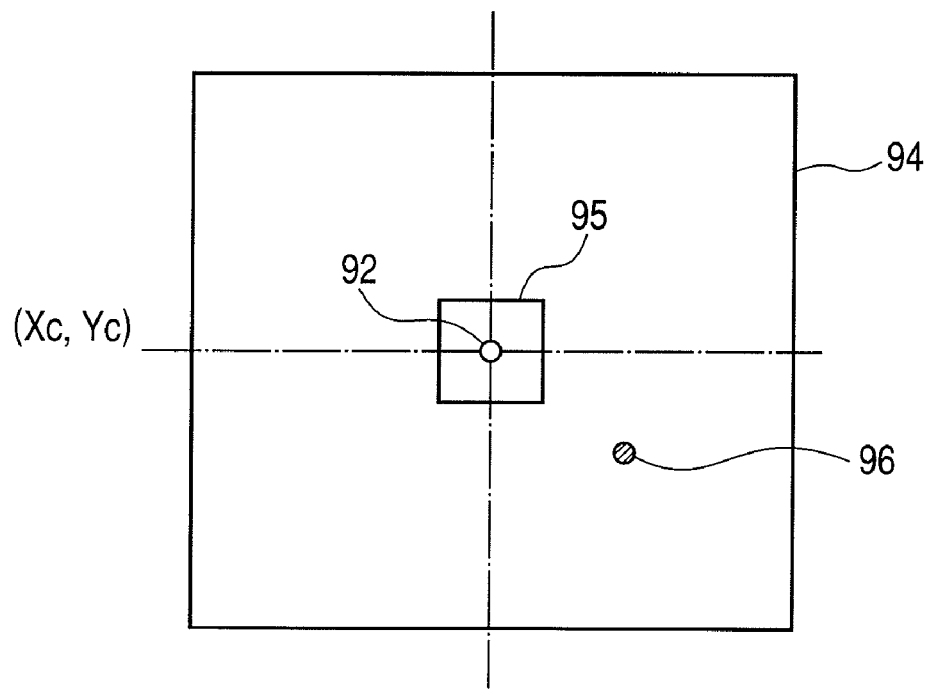
FIG. 8B is a diagram showing the relationship between the visual field of the optical microscope and the visual field of a scanning electron microscope.

Next, a description will be made of a method for redetection of the position of a defect by means of dark field illumination. The scattered light detected by the optical detection system 60a by means of the dark field illumination is imaged on the optical detector 62. For an image signal detected by the optical detector 62, analog-to-digital conversion is performed and the converted image signal is transferred (output) to the signal processing system 6. The signal processing system 6 sets a threshold value for the image signal. If a value of brightness of a certain pixel is larger than the threshold value, the certain pixel is deemed as a defect. When there are multiple defective pixels, the signal processing system 6 calculates a centroid pixel among the defective pixels to obtain an image signal 91 as shown in FIG. 8A. In the image signal 91 according to the present invention with reference to FIG. 8A, coordinates 93 indicating the precise position of a defect precisely re-detected by the optical microscope 5a are generated displacements for central coordinates 92 (Xc, Yc) corresponding to information on the rough position of a defect, which has been detected by the external optical inspection apparatus beforehand (in advance) and is stored in the database 10. As shown in FIG. 8B, the visual field 95 of the scanning electron microscope 4 is smaller than the visual field 94 of the optical microscope 5a. It takes a relatively long time to detect a defect 96 by the scanning electron microscope 4 from the central coordinates 92 (Xc, Yc) corresponding to the information on the rough position of the defect, which has been detected by the external optical inspection apparatus beforehand. The signal processing system 6 calculates coordinate differences (amount of displacements) Xs 97 and Ys 98 between the coordinates 93 indicating the precise position of the defect within the visual field 94 of the optical microscope 5a and the central coordinates 92 indicating the rough position of the defect which has been detected by the external optical inspection apparatus beforehand. The signal processing system 6 transmits to the total controller 8 the calculated values of displacements as corrected values of coordinates. The total controller 8 registers the corrected values of coordinates in the database 10 or the like. The signal processing system 6 may obtain each of the amount of displacements by calculating the number of pixels existed between the central coordinates 92 indicating the rough position of the defect and the coordinates 93 indicating the precise position of the defect and multiplying the calculated number of the pixels by each pixel size.

The total controller 8 provided in the apparatus for reviewing a defect according to the present invention corrects, for each defect, coordinate differences between coordinates indicating the rough position of a defect which has been detected by the external optical inspection apparatus beforehand and coordinates indicating the precise position of the defect actually redetected by the optical microscope 5a according to the present invention. In this case, after the optical microscope 5a redetects the first several defects, the optical microscope 5a does not subsequently redetect a defect when the following conditions are met: the abovementioned coordinate differences for each defect exhibit regularity; the distance of each horizontal movement is constant; and the amount of each rotational movement is constant. When the abovementioned conditions are met, the total controller 8 can correct coordinates indicating the rough position of a defect based on a correction formula created according to the regularity to obtain coordinates indicating the precise position of the defect for each defect.

Next, a description will be made of reviewing of a defect in detail by the scanning electron microscope (SEM) 4. After coordinate differences between coordinates indicating the rough position of a defect and coordinates indicating the precise position of the defect are corrected, the total controller 8 outputs a command to drive the XY stage 3 having the sample 1 thereon to ensure that the existing defect on the sample 1 is positioned on the optical axis 12 of the scanning electron microscope 4. After the defect is positioned on the optical axis 12, the SEM height detection system 7 detects the vertical position of the upper surface of the sample 1. An excitation current for an objective lens (not shown) provided in the scanning electron microscope 4 is controlled to adjust the focusing position of the scanning electron microscope 4. The scanning electron microscope 4 then acquires an SEM image at a low magnification for the defect. The scanning electron microscope 4 detects the position of the defect based on the SEM image acquired at the low magnification for the defect. The scanning electron microscope 4 scans a region centering on the detected defects to acquire an SEM image of the defect at a high magnification. The in-focus position for acquiring the SEM image at the high magnification, is adjusted by using SEM images obtained on each of the varied focus positions at the high magnification. The scanning electron microscope 4 transmits the SEM image acquired at the high magnification obtained on the adjusted in-focus position to the total controller 8. The total controller 8 then receives the SEM image and transmits the received SEM image to the input/output terminal 9 and the database 10. The input/output terminal 9 displays the SEM image. The SEM image is registered in the database 10. In addition, the total controller 8 analyzes the SEM image acquired at the high magnification to extract the defect and automatically classify the defect.

Next, a description will be made of the SEM height detection system 7 provided under the scanning electron microscope 4 with reference to FIG. 9. The SEM height detection system 7 includes a white light source 101, a slit light illumination optical system 100, a projection lens 104, and a detection lens 105. The white light source 101 is comprised of halogen lamp or the like. The slit light illumination optical system 100 includes a condenser lens 102 for converging white light and a slit plate 103 for forming slit light. The projection lens 104 is designed to image the slit light on the sample 1 as a slit image. The detection lens 105 is designed to image, on an optical detection element 106, the slit light specularly reflected on the sample 1 as a slit image. As shown in FIG. 9, the slit image imaged on the optical detection element 106 is shifted by a value of $2M \cdot \Delta Z \cdot \sin \theta$ when the sample 1 is moved by a value of distance (height) $\Delta Z$ in the vertical direction. In this case, an incident angle 107 of the slit light, which is formed between a direction of propagation of the slit light and the normal to the upper surface of the sample 1, is $\theta$, and a magnification of the detection lens 105 is M. The vertical position of the upper surface of the sample 1 can be calculated by detecting the value of $2M \cdot \Delta Z \cdot \sin \theta$, which is the difference (hereinafter referred to as a shift amount) between the position of the image imaged on the optical detection element 106 in the case where the sample 1 is not moved by the value of distance $\Delta Z$ and the position of the image imaged on the optical detection element 106 in the case where the sample 1 is moved by the value of distance $\Delta Z$.

The white light source 101 may be replaced with a laser light source for emitting light having a single wavelength or the like. Monochromatic light may be repeatedly reflected within a transparent film, resulting in the fact that slit light is shifted or interference occurs due to the variation of the thickness of the transparent film. This may increase the difference between reflectance of a portion of a pattern and reflectance of another portion of the pattern. The intensity distribution of the reflected light may be varied, and an erroneous value of the vertical position of the upper surface of the sample may be increased. The slit plate 103 may be replaced with a single slit. The optical detection element 106 may be a position sensor. It is possible to reduce the erroneous value of the vertical position of the upper surface of the sample due to the difference between reflectance of a portion of a pattern and reflectance of another portion of the pattern, when the slit plate 103 is a multi-slit having multiple slits, and the optical detection element 106 uses a CCD linear sensor and calculates the shift amount of the slit image by averaging the shift amount of each slit based on the waveform of light detected by the CCD linear sensor.

Figure 10:
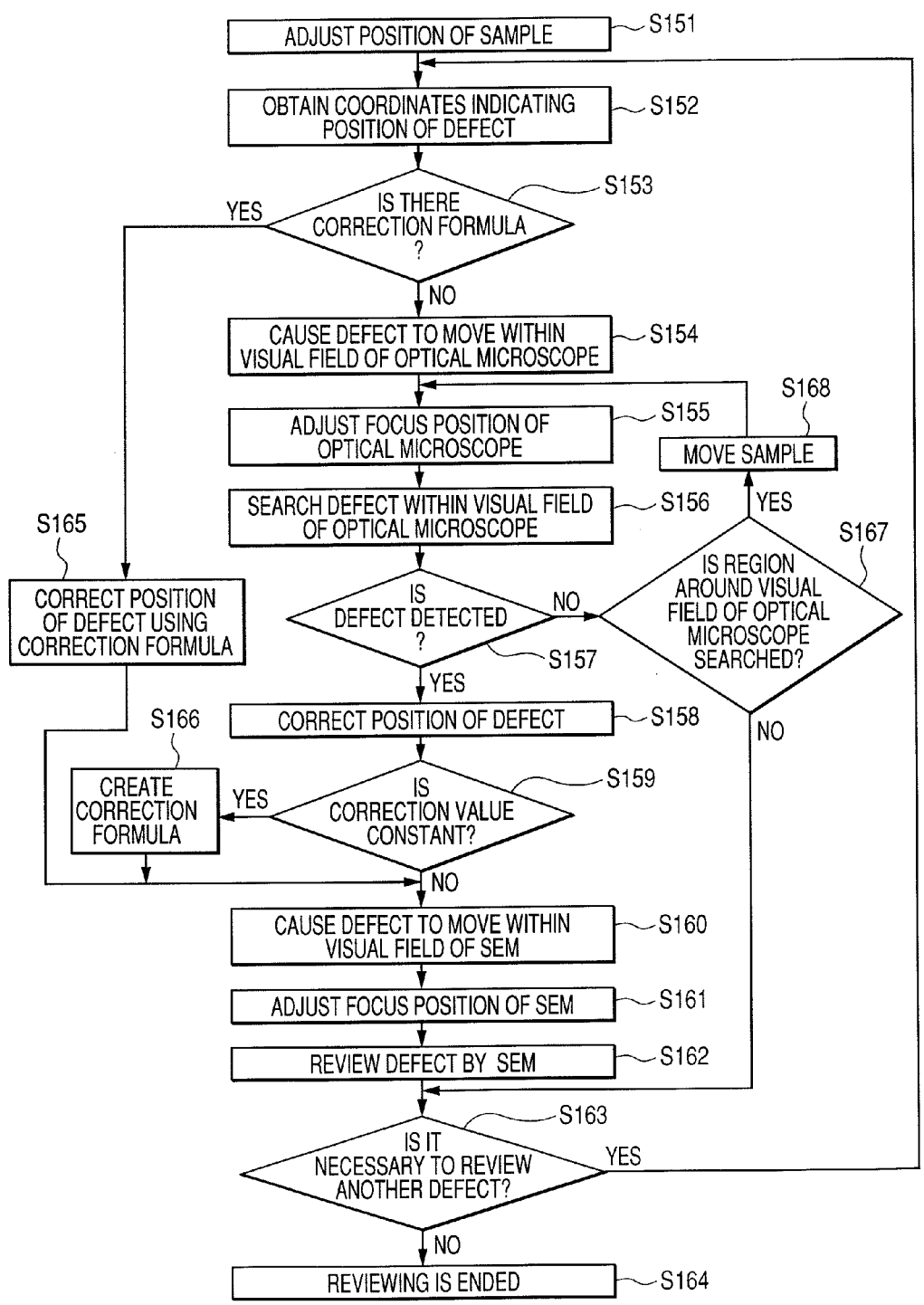
FIG. 10 is a flowchart showing a sequence of operations performed in the apparatus according to the first embodiment.

Next, a description will be made of operations of the apparatus for reviewing a defect according to the present invention with reference to FIG. 10. First, a existing defect on the sample 1 such as a semiconductor wafer, which is to be reviewed by the apparatus according to the present invention has been detected by the external optical inspection apparatus (the optical foreign material inspection apparatus or the like) having high throughput beforehand, and the rough position information of the existing defect on the sample 1, which has been detected by the external optical inspection apparatus, is input and stored in the database 10 or the like beforehand. The sample 1, on which the defect is inspected by the external optical inspection apparatus beforehand, is transferred into a load lock chamber (not shown). The load lock chamber is evacuated. After the evacuation, the sample 1 is transferred from the load lock chamber to the sample holder 2 provided in the vacuum chamber 13. Next, the total controller 8 causes the XY stage 3 to move to ensure that the sample 1 falls within the visual field of the optical microscope 5a.

In the optical microscope 5a, the bright field illumination light source 51 emits illumination light, and the illumination light is introduced through the inside of the microscope tube 40a to the edge portion of the microscope tube 40a. The illumination light is then illuminated on the sample 1 through the objective lens 46. In the optical microscope 5a, light reflected on the sample 1 is introduced through the microscope tube 40a to the optical detector 62. The optical detector 62 then detects the light reflected on the sample 1, generates an image signal indicating the sample 1 based on the light, and outputs the image signal to the signal processing system 6. The signal processing system 6 receives the image signal indicating the sample 1. The total controller 8 performs the alignment of the sample 1 based on the image signal received by the signal processing system 6 in step S151. In the alignment, image processing is performed for the received image signal to calculate XY shift amounts of the sample 1 and rotation amount (angle) of the sample 1. When the sample 1 has a pattern formed thereon, the total controller 8 calculates the XY shift amounts and the rotation amount of the sample 1 by processing the received image signal based on a predetermined pattern. When the sample 1 does not have a pattern, the total controller 8 calculates the XY shift amounts and the rotation amount of the sample 1 by processing the received image signal based on an edge portion of the sample 1. Based on the calculated shift amount and rotation amount, the total controller 8 aligns the sample 1 to the reference position of the optical microscope 5a.

After the alignment of the position of the sample 1 ends, the total controller 8 obtains coordinates indicating the rough position of the defect to be reviewed from the rough position information of the existing defect on the sample 1 includes a large detection error of the defect on the upper surface of the sample 1, which has been detected by the external optical inspection apparatus (not shown) and input and stored in the database 10 or the like beforehand in step S152. The total controller 8 then confirms whether or not there is a created correction formula for the coordinates indicating the rough position of the defect to be reviewed in step S153. The correction formula is created when the total controller 8 determines that the coordinate differences (the amount of displacements) between the coordinates indicating the precise position of a defect redetected by the optical microscope 5a for each of the first several defects and the coordinates indicating the rough position of the defect detected by the external optical inspection apparatus are constant or exhibit regularity. The correction formula is not created when the total controller 8 determines that the abovementioned coordinate differences are not constant or does not exhibit regularity.

When there is not a created correction formula, the total controller 8 causes the XY stage 3 to move to ensure that a existing defect on the sample 1 is positioned within the visual field of the optical microscope 5a for the defect based on the coordinates indicating the rough position of the defect in step S154. In this case, the coordinates indicating the rough position of each defect is already obtained in step S152. After the XY stage 3 is moved, the total controller 8 calculates a distance (height) $\Delta z$ based on the in-focus position of the upper surface of the sample 1 on the detection coordinates which the defect positioned within the visual field of the optical microscope 5a and drives the Z actuator 136 to move the microscope tube 40a in the vertical direction Z, thereby adjusting the in-focus position of the optical microscope 5a to the upper surface of the sample in step S155. The following value is used to adjust the in-focus position: the distance (height) $\Delta z$ is detected as the sift amount $\Delta s$ ($=2M \cdot \Delta z \cdot \tan \theta$) of the upper surface of the sample 1 based on the in-focus position by the OM height detection system 70a as shown in FIG. 2. Next, the signal processing system 6 causes the optical microscope 5a to search the position of the defect based on the image detected by the optical detector 62 comprised of a two-dimensional CCD camera or the like in step S156. The optical detector 62 is provided in the optical microscope 5a. The signal processing system 6 then performs redetection of a defect in step S157. When the defect is detected, the total controller 8 calculates the coordinate differences (amount of displacements) between the coordinates indicating the rough position of the defect which has been detected by the external optical inspection apparatus beforehand and the coordinates indicating the precise position of the defect within the visual field of the optical microscope 5a to correct the rough position information of the defect to the precise position information of the defect based on the calculated coordinate differences (amount of displacements) in step S158.

Next, the total controller 8 determines whether or not coordinate differences between the coordinates indicating the rough position of the defect detected by the other (external) optical inspection apparatus and the coordinates indicating the precise position of the defect redetected by the optical microscope 5a are constant or exhibit regularity in step S159. The operation in step S159 is performed after the optical microscope 5a redetects the first several defects. The operation in step S159 is not performed during the redetection of the first several defects by the optical microscope 5a. When the coordinate differences (which are to be corrected) are not constant, the total controller 8 causes the defect to move (fall) within the visual field of the scanning electron microscope 4 based on the corrected precise position information of the defect in step S160.

After that, the SEM height detection system 7 detects the vertical position of the upper surface of the sample 1. The total controller 8 performs the adjustment of the focus position by controlling the objective lens (not shown) provided in the scanning electron microscope 4 based on the vertical position of the upper surface of the sample 1 detected by the SEM height detection system 7, and further the adjustment of the focus position by using an SEM image acquired at a high magnification in step S161. The scanning electron microscope 4 irradiates an electron beam on the sample 1 to scan a region (set by the deflection electrode) of the upper surface of the sample 1. The scanning electron microscope 4 detects a secondary electron generated from the sample 1 or an electron reflected from the sample 1 to obtain a highly magnified image based on the secondary electron or the reflected electron. The total controller 8 reviews and classifies the defect based on the highly magnified SEM image indicating the defect acquired by the scanning electron microscope 4 in step S162.

Next, the total controller 8 determines whether or not it is necessary to review another defect in step S163. If it is not necessary, the reviewing is ended in step S164. If it is necessary, the process proceeds back to step S152 of obtaining the rough position information of the other defect. The operations in steps S153 to S162 are repeated.

When the total controller 8 confirms that there is a correction formula in step S153, the rough position information of the defect is corrected according to the correction formula. In this case, the optical microscope 5a does not redetect the defect. The process then proceeds to step S160 of causing the defect to move within the visual field of the scanning electron microscope 4 based on the corrected precise position information of the defect. When the signal processing system 6 cannot detect a defect in step S157 after step S156 in which the signal processing system 6 causes the optical microscope 5a to search the position of the defect based on the image detected by the optical detector 62 provided in the optical microscope 5a, the signal processing system 6 determines whether or not the signal processing system 6 causes the optical microscope 5a to search a region (of the upper surface of the sample 1) around the visual field of the optical microscope 5a in step S167. If the signal processing system 6 causes the optical microscope 5a to search the region around the visual field of the optical microscope 5a based on the result of the determination in step S167, the total controller 8 causes the sample 1 to move in step S168. After step S168, the process proceeds back to step S155 of adjusting the focus position of the optical microscope 5a based on the vertical position of the upper surface of the sample 1 detected by the OM height detection system 70a. After step S155, steps S156 and S157 are repeated until a defect is detected. If the signal processing system 6 does not cause the optical microscope 5a to search the region around the visual field of the optical microscope 5a, the process proceeds to step S163, in which the total controller 8 determines whether or not it is necessary to review another defect.

In the abovementioned process, the total controller 8 determines whether or not the abovementioned coordinate differences are constant or exhibit regularity in step S159 for the first several defects when the defect was detected. The total controller 8 may determine whether or not the coordinate differences are constant or exhibit regularity by redetecting some defects which exist around main points determined beforehand on the entire upper surface of the sample 1, before the operation in step 152 is performed.

In the abovementioned process, the vertical position of the upper surface of the sample 1 is detected twice for adjustment of the focus position of the optical microscope 5a and adjustment of the focus position of the scanning electron microscope 4. It can be considered that the vertical position of the upper surface of the sample 1 is detected for either the adjustment of the focus position of the optical microscope 5a or the adjustment of the focus position of the scanning electron microscope 4. Alternatively, it can be considered that the vertical position of the sample 1 is detected once at another common position on the stage between the optical microscope 5a and the scanning electron microscope 4. When such a correction formula to be used in the abovementioned sequence is used, the optical microscope 5a does not redetect a defect. When the optical microscope 5a searches a region around the visual field thereof in order to redetect a defect, the optical microscope 5a continuously reviews the sample 1. In this case, the sample 1 is not moved to the scanning electron microscope 4. In the case where either one of the scanning electron microscope 4 and the optical microscope 5a continuously detects defects or reviews the sample 1, each of the microscopes 4 and 5a detects the vertical position of the upper surface of the sample 1. This makes it possible to increase the throughput for reviewing a defect. In the case where the optical microscope 5a detects a defect and the scanning electron microscope 4 reviews the sample 1 in a continuous process, each of the microscopes 5a and 4 detects the vertical position of the upper surface of the sample 1. This reduces an error of the vertical position of the upper surface of the sample 1 due to the positional difference between the position of the stage in the case of the detection performed by the scanning electron microscope 4 and the position of the stage in the case of the detection performed by the optical microscope 5a, resulting in an improvement in accuracy of the detection.

Second Embodiment

Figure 11:
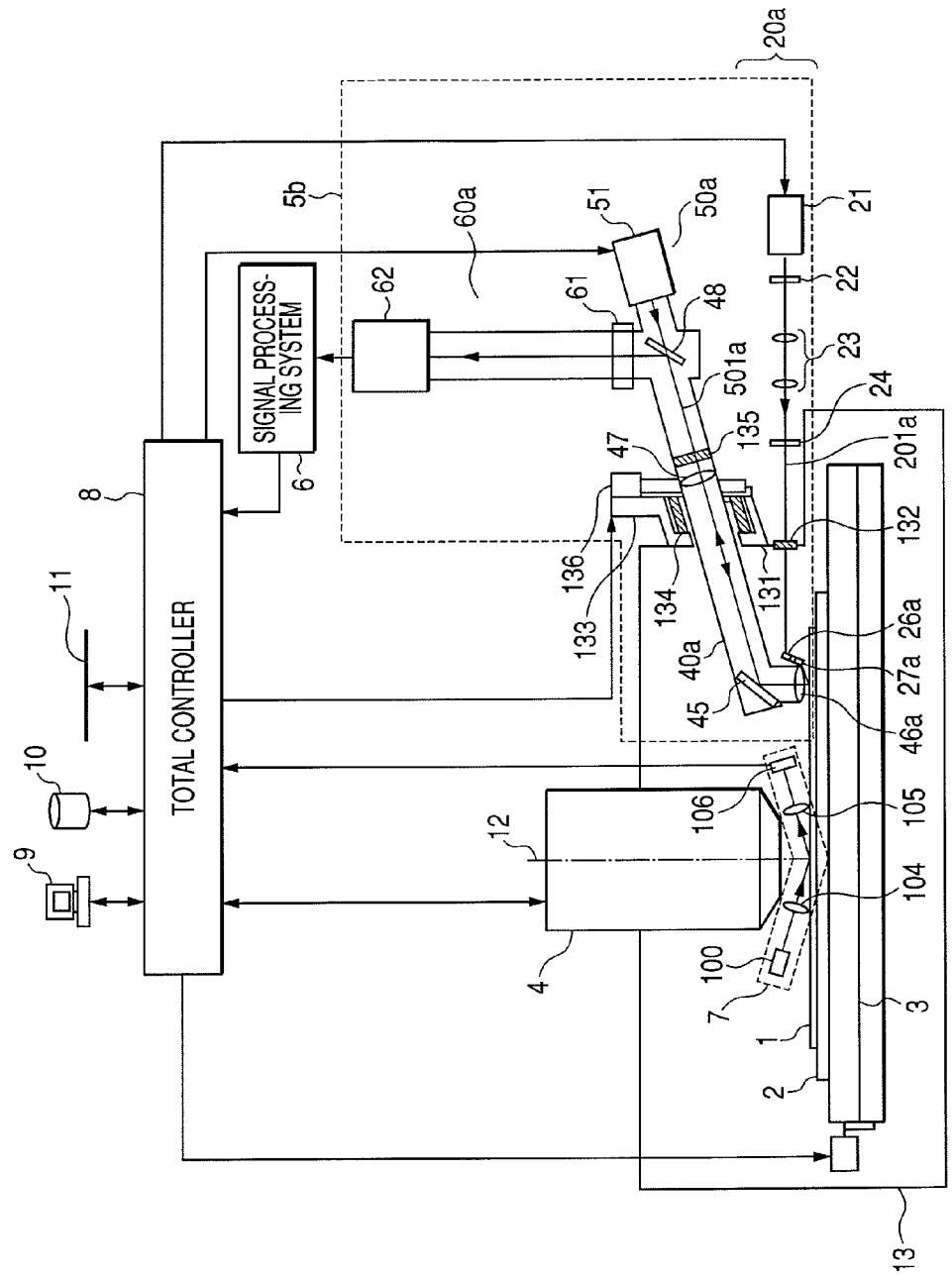
FIG. 11 is a diagram showing an outline construction of an apparatus for reviewing a defect according to a second embodiment of the present invention.

Next, a description will be made of an apparatus for reviewing a defect according to a second embodiment of the present invention with reference to FIG. 11. In the second embodiment, an optical microscope 5b does not include the OM height detection system 70a, and the SEM height detection system 7 provided under the scanning electron microscope 4 is used to adjust the focal point of the optical microscope 5b. Other features of the second embodiment are the same as those of the first embodiment.

Figure 12:
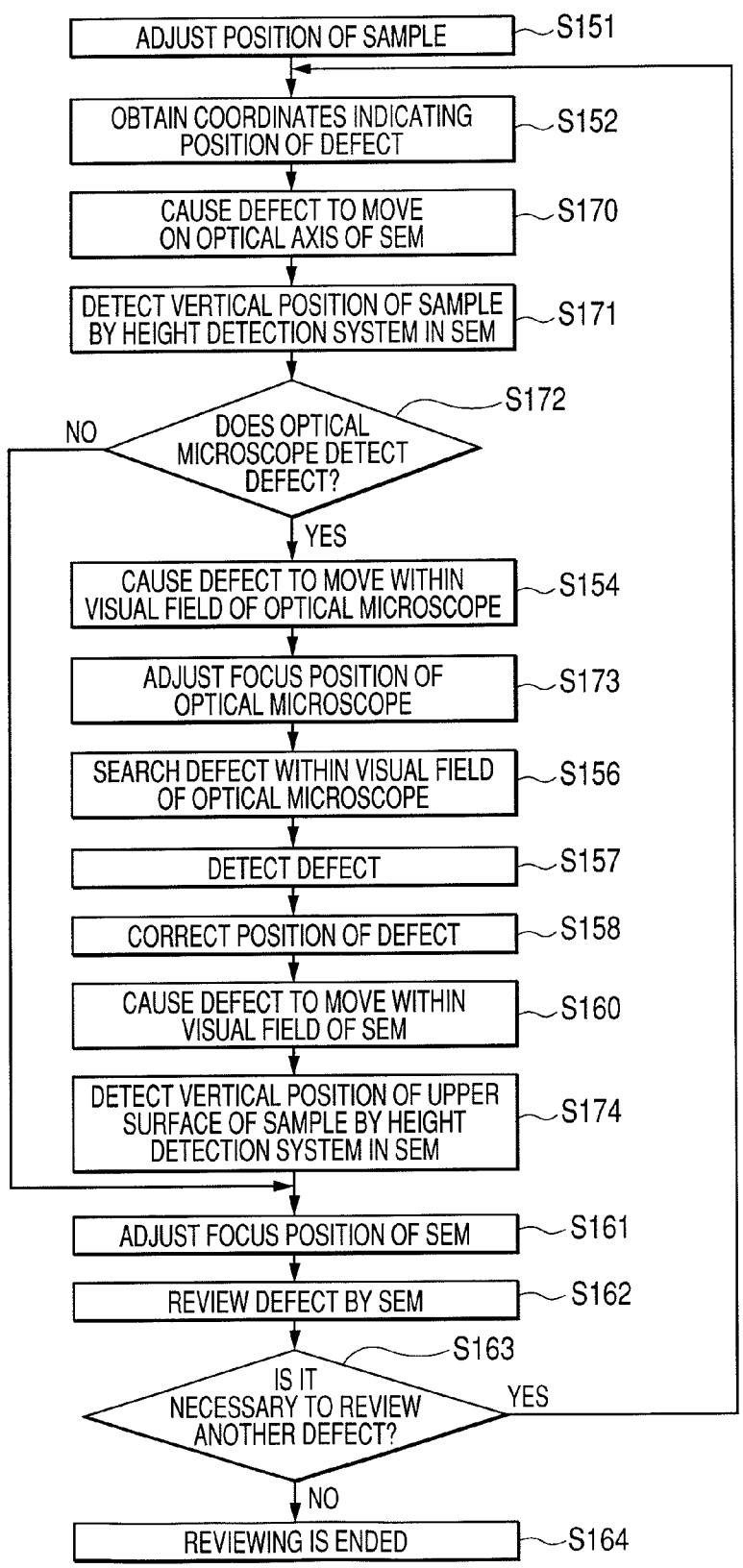
FIG. 12 is a flowchart showing a sequence of operations performed in the apparatus according to the second embodiment.

Referring to FIG. 12, a description will be made of a process for reviewing a defect in the apparatus according to the second embodiment of the present invention. Since the optical microscope 5b does not include the OM height detection system 70a, the optical microscope 5b uses the SEM height detection system 7 to detect the vertical position of the upper surface of the sample 1. This feature is different from that in the first embodiment. In the second embodiment, after the rough position information of a defect is obtained, the total controller 8 causes the defect to move to the optical axis of the scanning electron microscope 4 provided with the SEM height detection system 7 based on the rough position information of the defect in step S170, as shown in FIG. 12. The SEM height detection system 7 detects the vertical position of the upper surface of the sample 1 in step S171. The total controller 8 then determines whether or not the optical microscope 5b redetects the defect in step S172. When the total controller 8 determines that the optical microscope 5b redetects the defect in step S172, the total controller 8 causes the existing defect on the sample 1 to move within the visual field of the optical microscope 5b based on the rough position information of the defect in step S154. The total controller 8 drives the Z actuator 136 based on the vertical position of the upper surface of the sample 1 detected by the SEM height detection system 7 to adjust the focus position of the optical microscope 5b in step S173. Steps S156 to S160 and step S174 in the second embodiment are the same as those in the first embodiment. When the controller 8 determines that the optical microscope 5b does not redetect the defect in step S172, the process proceeds to step S161. Steps S161 to S164 in the second embodiment are the same as those in the first embodiment.

In the second embodiment, only the SEM height detection system 7 provided under the scanning electron microscope 4 detects the vertical position of the upper surface of the sample 1. To continuously detect defects by means of the optical microscope 5b without reviewing the defects by the scanning electron microscope 4, it is necessary that the sample 1 is moved to the optical axis 12 of the scanning electron microscope 4 in order to detect the vertical position of the upper surface of the sample 1. This reduces the throughput. To avoid this problem, the following methods are adopted in the second embodiments. In the first method, the SEM height detection system 7 measures the vertical position of the upper surface of the sample 1 at main points on the entire upper surface of the sample 1 to create a map of the vertical position of the upper surface of the sample 1. The map is interpolated based on the coordinates indicating the rough position of the defect detected by the external optical inspection system. When the optical microscope 5b continuously redetects defects, the focus position of the optical microscope 5b is adjusted based on the interpolated map of the vertical position of the upper surface of the sample 1. In the second method, when points of coordinates indicating the rough positions of defects to be sequentially detected are close to each other, the difference between the vertical positions of the upper surface of the sample 1 at the points is small. In this case, the vertical positions of the sample 1 at the points are deemed as the same vertical position. Alternatively, a change in the vertical position of the upper surface of the sample 1 is calculated based on inclination set for each direction of movement of the sample 1, and the focus position of the optical microscope 5b is adjusted based on the change in the vertical position of the upper surface of the sample 1.

Using the vertical position of the upper surface of the sample 1 obtained in the abovementioned first or second method as a starting point, the Z actuator 136 is driven to move the optical detection system 60a and the microscope tube 40a at a certain step while the optical detector 62 detects an image indicating the sample 1. A point at which contrast of the detected image is the maximum is deemed as the focus position of the optical microscope 5b. This makes it possible to adjust the focus position of the optical microscope 5b with high precision. In this case, a value close to the actual vertical position of the upper surface of the sample 1 is used as a starting point, the number of steps of moving the optical detection system 60a in the Z direction can be reduced compared with the case where the starting point is not used. This results in a reduction in the time for adjusting the focal point of the optical microscope 5b.

Third Embodiment

Figure 13:
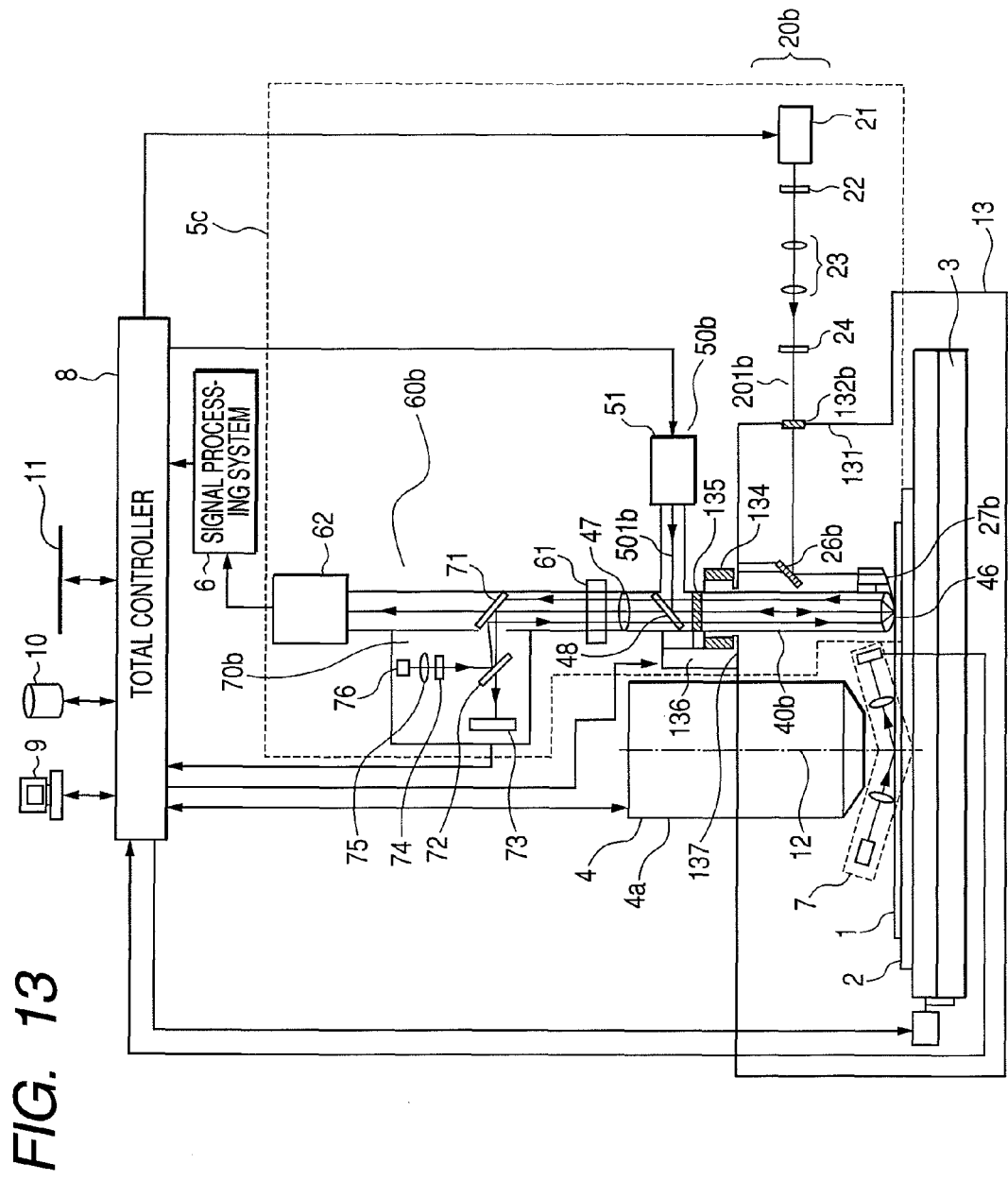
FIG. 13 is a diagram showing an outline construction of an apparatus for reviewing a defect according to a third embodiment of the present invention.

Next, a description will be made of an apparatus for reviewing a defect according to a third embodiment of the present invention with reference to FIG. 13. In the third embodiment, a microscope tube 40b is provided at an edge portion of an optical microscope 5c and in the vacuum chamber 13, and attached to an upper wall 137 of the vacuum chamber 13. The microscope tube 40b is designed to extend in the vertical direction perpendicular to the upper surface of the XY stage 3. Components for controlling parts provided in the microscope tube 4a are provided above the upper wall 137 of the vacuum chamber 13 and around the microscope tube 4a of the scanning electron microscope 4. It is, therefore, difficult that the microscope tube 40b (extending in the vertical direction of the optical microscope 5c) is arranged closely to the microscope tube 4a of the scanning electron microscope 4 as compared with that of the first embodiment. It is, however, possible that the microscope tube 4a has a space in which the objective lens 46 having a large numerical aperture is provided at an edge portion of the microscope tube 40b since a mirror (an optical element) or the like for changing a direction of propagation of light is not provided in the microscope tube 40b.

The optical microscope 5c includes a dark field illumination optical system 20b, which emits dark field illumination light 201b. The dark field illumination light 201b is incident on the edge portion of the microscope tube 40b provided in the vacuum chamber 13 through a transparent window (a vacuum blocking glass) 132b provided on a side wall 131 of the vacuum chamber 13. The bright field illumination light source 51 emits bright field illumination light 501b. The bright field illumination light 501b is introduced to the edge portion of the microscope tube 40b in the vacuum chamber 13 through a transparent window (a vacuum blocking glass) 135. Light reflected on or scattered from the sample 1 passes through the microscope tube 40b and the transparent window (vacuum blocking glass) 135 and is introduced to the outside of the vacuum chamber 13. The light is then detected by the optical detector 62. To fix the microscope tube 40b to the Z actuator 136 attached to the upper wall 137 of the vacuum chamber 13 and maintain degree of vacuum within the vacuum chamber 13, a bellows 134 is provided between the microscope tube 40b and the upper wall 137 of the vacuum chamber 13. As apparent from the above description, a portion of a bright field illumination optical system 50b, a portion of an optical detection system 60b and a portion of an optical microscope (OM) height detection system 70b are shared with the microscope tube 40b. The microscope tube 40b is provided with the objective lens 46, the beam splitter 48, the imaging lens 47 and a prism (reflecting optical element) 27b. The objective lens 46 provided in the microscope tube 40b converges light from the side of the edge portion of the microscope tube 40b. The prism 27b is provided at the edge portion of the microscope tube 40b and used for dark field illumination. A prism (mirror) (reflecting optical element) 26b, which is to be used for the dark field illumination, is fixed to the vacuum chamber 13.

The dark field illumination optical system 20b according to the third embodiment is different from the dark field illumination optical system 20a in the relative position of the mirror 26b fixed to the vacuum chamber 13 to the microscope tube 40b and the position of the prism 27b attached to the edge portion of the microscope tube 40b. The other features of the dark field illumination optical system 20b are the same as those of the dark field illumination optical system 20a according to the first embodiment. In the bright field illumination optical system 50b, the bright field illumination light source 51 emits bright field illumination light 501b such as white light to the beam splitter 48 from a direction perpendicular to the vertical direction. The bright field illumination light 501b then propagates into the microscope tube 40b. This feature of the bright field illumination optical system 50b is different from the bright field illumination optical system 50a according to the first embodiment. The other features of the bright field illumination optical system 50b are the same as those of the bright field illumination optical system 50a according to the first embodiment. In the optical detection system 60b, the microscope tube 40b is designed to extend in the vertical direction. The other features of the optical detection system 60b are the same as those of the optical detection system 60a according to the first embodiment, and the other features of the OM height detection system 70b are the same as those of the OM height detection system 70a according to the first embodiment.

In the third embodiment, the Z actuator 136 is driven based on the vertical position of the upper surface of the sample 1 detected by the OM height detection system 70b to slightly move the entire microscope tube 40b and the optical detection system 60b in the z direction in order to ensure that the focus position of the optical microscope 5c is existed on the upper surface of the sample 1.

Since the imaging lens 47 has a fixed focal length, a magnification of the optical detection system 60b is constant. A zoom lens may be used for the imaging lens 47 to change the magnification of the optical detection system 60b. When the magnification of the optical detection system 60b is changed, it is necessary that a magnification to be used for calculation of the vertical position of the upper surface of the sample be changed in order to detect the vertical position of the upper surface of the sample by means of the OM height detection system 70b.

Fourth Embodiment

Figure 14:
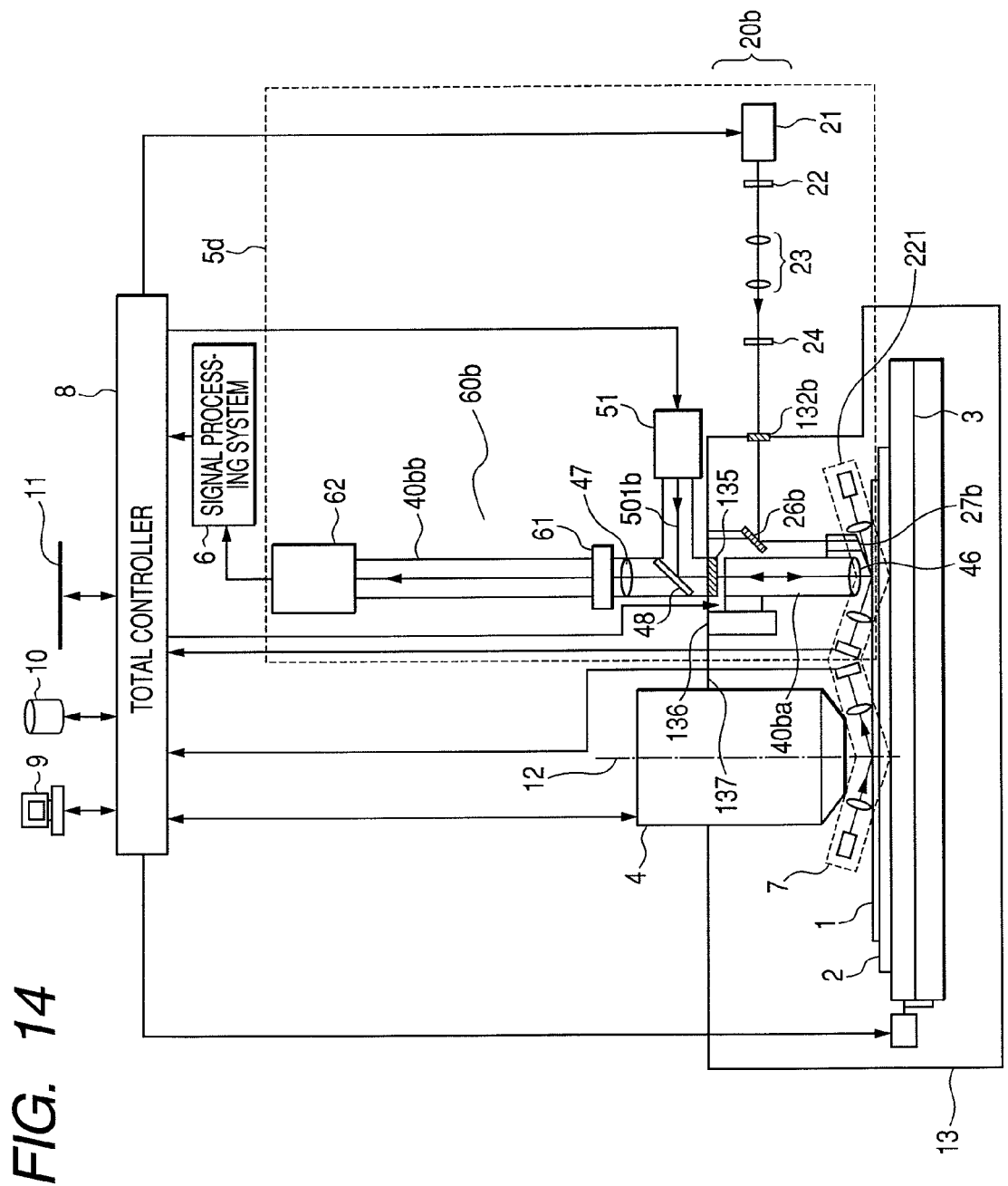
FIG. 14 is a diagram showing an outline construction of an apparatus for reviewing a defect according to a fourth embodiment of the present invention.

Next, a description will be made of an apparatus for reviewing a defect according to a fourth embodiment of the present invention with reference to FIG. 14. In the fourth embodiment, the OM height detection system 70b is not provided in an optical microscope 5d. The microscope tube 40b is divided into a lower part 40ba and an upper part 40bb at a boundary at which the transparent window (vacuum blocking glass) 135 is existed in the fourth embodiment. The transparent window 135 is provided on the upper wall 137 of the vacuum chamber 13. The lower part 40ba of the microscope tube 40b includes the objective lens 46 provided in the vacuum chamber 13. The upper part 40bb of the microscope tube 40b is provided above the vacuum chamber 13. The Z actuator 136, which is attached to the upper wall 137 of the vacuum chamber 13, is driven to allow only the lower part 40ba and the objective lens 46 of the microscope tube 40b provided in the vacuum chamber 13 to move (although the Z actuator 136 is driven to move the entire microscope tube 40b and the optical detection system 60b in the third embodiment). The configuration of the apparatus according to the fourth embodiment is therefore simple. In the fourth embodiment, an off axis method is used. In the off axis method, an off axis optical height detection system 221 optically detects the vertical position of the upper surface of the sample 1 from a direction inclined to the optical axis of the lower part 40ba of the microscope tube 40b. The off axis optical height detection system 221 is located under the optical microscope 5d. In the fourth embodiment, slit light is not detected through the objective lens 46 (although slit light is detected through the objective lens 46 in the third embodiment). In the off axis method, the incident angle of the slit light for detecting the vertical position of the upper surface of the sample 1 with respect to the normal to the upper surface of the sample 1 can be large. When the sample 1 has a transparent film formed thereon, an error of the vertical position of the upper surface of the sample 1 due to multiple reflections can be reduced. In the apparatus according to the fourth embodiment of the present invention, the off axis optical height detection system 221 is provided in place of the OM height detection system 70b according to the third embodiment, and the microscope tube 40b is divided into the lower part 40ba and the upper part 40bb. The other features of the apparatus according to the fourth embodiment are the same as those of the apparatus according to the third embodiment. The off axis optical height detection system 221 is basically the same as the SEM height detection system 7 in the first embodiment. In the off axis optical height detection system 221, a white light source or a laser may be used as a light source, a slit plate having a single slit or a slit plate having multiple slits may be used, and a position sensor or a CCD linear sensor may be used as an optical sensor, based on detection accuracy, a unoccupied space and the like. In the fourth embodiment, the Z actuator 136 is driven to ensure that the lower part 40ba of the microscope tube 40b and the objective lens 46 provided in the microscope tube 40b are moved in the Z direction to cause the focus position of the optical microscope 5d to be existed on the upper surface of the sample 1, while the upper part 40bb of the microscope tube 40b is fixed and does not move. The vertical position of the sample 1 is detected by the off axis method with high precision.

In the first to fourth embodiments, the focal point of the scanning electron microscope 4 is adjusted by adjusting an excitation current or the like for the objective lens, and the focus position of each of the optical microscopes 5a to 5d is adjusted by moving the respective microscope tubes 40a, 40b and 40ba provided with the respective optical detection system 60a and 60b in the Z direction, based on the vertical position of the upper surface of the sample obtained by the respective height detection systems 7, 70a, 70b and 221. The height detection system 7 is provided under the scanning electron microscope 4. The height detection systems 70a, 70b and 221 are provided in the optical microscopes 5a, 5c and 5d, respectively. The stage, however, may have a drive mechanism for moving the stage in the Z direction in the first to fourth embodiments. The drive mechanism is capable of causing the stage to move in the Z direction to adjust the focal point based on the vertical position of the upper surface of the sample obtained by any of the height detection systems to adjust the focus position of any of the scanning electron microscope 4 and the optical microscopes 5a to 5d.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An apparatus for reviewing a defect, comprising:
a vacuum chamber;
a stage provided in the vacuum chamber;
an optical microscope configured to optically re-detect an existing defect on a sample placed on the stage, the existing defect being previously detected by an external optical inspection apparatus, and configured to obtain position information of the existing defect on the sample;
a correction means configured to correct position information of the existing defect on the sample, the existing defect being previously detected by the external optical inspection apparatus, the position information correction being based on the position information obtained by optical re-detection of the existing defect on the sample by the optical microscope; and
a scanning electron microscope configured to review the existing defect on the sample by positioning the existing defect on the sample within a visual field of the scanning electron microscope by moving the stage based on the position information of the existing defect corrected by the correction means;
wherein the optical microscope includes:
an optical height detection system configured to optically detect a vertical position of an upper surface of the sample placed on the stage;
an illumination optical system configured to illuminate the existing defect on the sample with light;
an image detection optical system configured to converge and detect reflected light or scattered light generated from the existing defect on the sample illuminated by the illumination optical system, and to obtain an image signal; and
a focus adjusting means configured to adjust a focus position of the optical microscope based on the vertical position of the upper surface of the sample, the vertical position being detected by the optical height detection system; and
wherein the optical height detection system, the illumination optical system, and the image detection optical system all use a common objective lens to detect an existing defect on the sample in the same location where the height is detected.

2. The apparatus according to claim 1, wherein
the optical height detection system of the optical microscope is configured to project slit light on the sample through an objective lens provided for the optical microscope, to detect slit reflection light reflected on the sample due to the projection of the slit light by an optical sensor through the objective lens, and to detect a vertical position of the upper surface of the sample based on position of the slit reflection light detected by the optical sensor.

3. The apparatus according to claim 1, wherein
the illumination optical system of the optical microscope is comprised of a dark field illumination optical system configured to illuminate the existing defect on the sample with the light from a direction that inclines to the upper surface of the sample.

4. The apparatus according to claim 3, wherein
the image detection optical system of the optical microscope has a polarization detector configured to detect a polarization direction different from a polarization direction of the light output from the dark field illumination optical system.

5. An apparatus for reviewing a defect, comprising:
a vacuum chamber;
a stage provided in the vacuum chamber;
an optical height detection system configured to optically detect a vertical position of an upper surface of a sample placed on the stage;
an optical microscope configured to optically re-detect an existing defect on the sample placed on the stage, the existing defect being previously detected by an external optical inspection apparatus, and configured to obtain position information of the existing defect on the sample;

a correction means configured to correct position information of the existing defect on the sample, the existing defect being previously detected by the external optical inspection apparatus, the correction of position information being based on the position information obtained by optical re-detection of the existing defect on the sample by the optical microscope; and a scanning electron microscope configured to review the existing defect on the sample placed on the stage, by positioning the existing defect on the sample within a visual field of the scanning electron microscope by moving the stage based on the position information of the existing defect corrected by the correction means;

wherein the optical microscope includes:
- an illumination optical system configured to illuminate the existing defect on the sample with light;
- an image detection optical system configured to converge and detect reflected light or scattered light generated from the existing defect on the sample illuminated by the illumination optical system, thereby obtaining an image signal; and
- a focus adjusting means configured to adjust a focus position of the optical microscope, based on the vertical position of the upper surface of the sample, is the vertical position being detected by the optical height detection system;

wherein the illumination optical system and the image detection optical system of the optical microscope, and the optical height detection system, all use a common objective lens to detect a existing defect on the sample in the same location where the height is detected.

6. The apparatus according to claim 5, wherein the optical height detection system configured to project slit light on the sample from a direction that inclines to the upper surface of the sample, to detect slit reflection light reflected on the sample due to the projection of the slit light by an optical sensor located diagonally above the point where the slit reflection light is reflected, and to detect a vertical position of the upper surface of the sample based on the position of the slit refection light detected by the optical sensor.

7. The apparatus according to claim 5, wherein the illumination optical system is comprised of a dark field illumination optical system configured to illuminate the existing defect on the sample with light from a direction that inclines to the upper surface of the sample.

8. A method for reviewing a defect, comprising the steps of:
obtaining position information of a defect on a sample placed on a stage provided in a vacuum chamber by optically re-detecting the existing defect on the sample with an optical microscope, the existing defect being previously detected by an external optical inspection apparatus;

correcting position information of the existing defect on the sample, the existing defect being previously detected by the external optical inspection apparatus, and the corrected position information being based on the position information obtained by optically re-detecting with the optical microscope; and reviewing the existing defect on the sample with a scanning electron microscope by positioning the existing defect on the sample within a visual field of the scanning electron microscope by moving the stage based on the corrected position information of the defect existing defect on the sample;

wherein the step of obtaining position information of a defect on a sample includes:
- optically detecting a vertical position of an upper surface of the sample placed on the stage with an optical height detection system, and
- adjusting a focus position of the optical microscope based on the detected vertical position of the upper surface of the sample;

wherein the steps of obtaining position information of a defect, optically re-detecting the existing defect, and optically detecting a vertical position, are performed including detecting light reflected from the sample and passed through an objective lens common to the optical microscope and the optical height detection system, to detect a existing defect on the sample in the same location where the height is detected.

9. A method for reviewing a defect, the defect being previously detected by an external optical inspection apparatus, the method comprises the steps of:
obtaining a precise position information of a defect on a sample placed on a stage provided in a vacuum chamber by illuminating with an optical microscope the defect on the sample with illumination light, and optically re-detecting the defect on the sample;

correcting rough position information of the defect on the sample, the defect being previously detected by the external optical inspection apparatus, based on the precise position information obtained by optically re-detecting with the optical microscope; and reviewing the defect on the sample with a scanning electron microscope by positioning the defect on the sample within a visual field of the scanning electron microscope, by moving the stage based on the corrected position information of the defect on the sample;

wherein in the obtaining step, a polarization direction of light used in optically re-detecting the defect on the sample is different from a polarization direction of the illumination light; and wherein in the obtaining step, a focus position of the optical microscope is adjusted by a focus adjusting means, based on a vertical position information of an upper surface of the sample detected by an optical height detection system through an objective lens common to the optical microscope and the optical height detection system to detect a defect on the sample in the same location where the height is detected.

* * * * *